(12) United States Patent
Kishimoto

(10) Patent No.: US 11,567,008 B2
(45) Date of Patent: Jan. 31, 2023

(54) IMMUNOSTAINING METHOD, IMMUNOSTAINING SYSTEM, AND IMMUNOSTAINING KIT

(71) Applicant: Sony Corporation, Tokyo (JP)

(72) Inventor: Takuya Kishimoto, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 16/957,239

(22) PCT Filed: Oct. 24, 2019

(86) PCT No.: PCT/JP2019/041633
§ 371 (c)(1),
(2) Date: Jun. 23, 2020

(87) PCT Pub. No.: WO2020/090600
PCT Pub. Date: May 7, 2020

(65) Prior Publication Data
US 2021/0364436 A1 Nov. 25, 2021

(30) Foreign Application Priority Data
Oct. 31, 2018 (JP) ............... JP2018-205977

(51) Int. Cl.
G01N 21/64 (2006.01)
G01N 1/30 (2006.01)
G01N 33/543 (2006.01)

(52) U.S. Cl.
CPC ........... G01N 21/6428 (2013.01); G01N 1/30 (2013.01); G01N 33/54306 (2013.01); G01N 21/6458 (2013.01)

(58) Field of Classification Search
CPC ............ H01L 51/5044; G01N 21/6489; G01N 21/6408
See application file for complete search history.

(56) References Cited

U.S. PATENT DOCUMENTS 4,822,733 A * 4/1989 Morrison ............. G01N 33/542
436/805
5,196,306 A   3/1993 Bobrow et al.
(Continued)

FOREIGN PATENT DOCUMENTS

EP   3 270 160 A1   1/2018
JP   06-109734      4/1994
(Continued)

OTHER PUBLICATIONS

International Search Report and English translation thereof dated Jan. 28, 2020 in connection with International Application No. PCT/JP2019/041633.

Primary Examiner — David P Porta
Assistant Examiner — Djura Malevic
(74) Attorney, Agent, or Firm — Wolf, Greenfield & Sacks, P.C.

(57) ABSTRACT

An immunostaining method includes an irradiation process in which a specimen, which includes a target molecule including an electron donor, an antibody that is bound to the target molecule and that includes a generating agent for generating active species when irradiated with a first excitation light, and a pigment compound, is irradiated with the first excitation light; and in which the pigment compound and the electron donor are bound due to the active species generated from the generating agent when irradiated with the first excitation light.

13 Claims, 16 Drawing Sheets

(56) References Cited

U.S. PATENT DOCUMENTS

| | | | |
|---|---|---|---|
| 5,583,001 A | 12/1996 | Bobrow et al. | |
| 5,731,158 A | 3/1998 | Bobrow et al. | |
| 5,874,046 A * | 2/1999 | Megerle | C12Q 1/6825 |
| | | | 422/50 |
| 6,406,914 B1 * | 6/2002 | Kaburaki | G01T 1/04 |
| | | | 436/1 |
| 7,173,702 B2 * | 2/2007 | Maurer | G01N 21/6486 |
| | | | 356/417 |
| 7,611,907 B2 * | 11/2009 | Dickson | G01N 33/588 |
| | | | 436/805 |
| 7,777,233 B2 * | 8/2010 | Kahen | C09K 11/883 |
| | | | 257/89 |
| 7,812,324 B2 * | 10/2010 | Connally | G01N 21/6408 |
| | | | 250/461.1 |
| 8,007,999 B2 * | 8/2011 | Holmes | C12Q 1/701 |
| | | | 435/5 |
| 8,323,221 B2 * | 12/2012 | Hall | C09K 19/38 |
| | | | 601/2 |
| 8,435,735 B2 * | 5/2013 | Lohse | C08G 63/672 |
| | | | 536/26.6 |
| 8,802,447 B2 * | 8/2014 | Swager | G01N 33/442 |
| | | | 436/524 |
| 9,404,870 B2 * | 8/2016 | Butte | G01N 21/6428 |
| 9,968,258 B2 * | 5/2018 | Guo | G01N 21/6486 |
| 10,021,747 B2 * | 7/2018 | Powers | H05B 45/44 |
| 10,041,883 B2 * | 8/2018 | Grundfest | G01N 21/6447 |
| 10,191,267 B2 * | 1/2019 | Endo | G02B 21/08 |
| 10,288,567 B2 * | 5/2019 | Butte | A61B 5/0071 |
| 10,596,387 B2 * | 3/2020 | Walder | A61K 49/0423 |
| 10,670,526 B2 * | 6/2020 | Xu | C12Q 1/6869 |
| 10,761,039 B2 * | 9/2020 | Heissenstein | G01N 25/72 |
| 2005/0089890 A1 * | 4/2005 | Cubicciotti | C07H 21/00 |
| | | | 530/395 |
| 2006/0014237 A1 * | 1/2006 | Maurer | C12M 41/36 |
| | | | 435/287.1 |
| 2006/0051878 A1 * | 3/2006 | Dickson | G01N 33/588 |
| | | | 436/518 |
| 2007/0117208 A1 * | 5/2007 | Niwa | C09K 11/7774 |
| | | | 436/166 |
| 2007/0264629 A1 * | 11/2007 | Holmes | B01L 3/5027 |
| | | | 435/5 |
| 2008/0085566 A1 * | 4/2008 | Swager | G01N 33/442 |
| | | | 428/407 |
| 2008/0118934 A1 * | 5/2008 | Gerdes | C12Q 1/6816 |
| | | | 436/503 |
| 2008/0265177 A1 * | 10/2008 | Connally | G01N 21/6458 |
| | | | 250/461.2 |
| 2009/0109435 A1 * | 4/2009 | Kahen | C09K 11/883 |
| | | | 313/503 |
| 2010/0240047 A1 * | 9/2010 | Lohse | G01N 33/54393 |
| | | | 435/5 |
| 2010/0240085 A1 * | 9/2010 | Lohse | C12Q 1/28 |
| | | | 435/28 |
| 2011/0097723 A1 * | 4/2011 | Liu | B82Y 15/00 |
| | | | 977/773 |
| 2011/0098609 A1 * | 4/2011 | Hall | A61N 7/02 |
| | | | 601/2 |
| 2011/0262897 A1 * | 10/2011 | Williams | A61K 49/001 |
| | | | 435/7.1 |
| 2012/0171668 A1 | 7/2012 | May et al. | |
| 2012/0252685 A1 * | 10/2012 | Treynor | G01N 33/6803 |
| | | | 435/6.19 |
| 2014/0024024 A1 * | 1/2014 | Sood | C12Q 1/6804 |
| | | | 435/6.11 |
| 2015/0031138 A1 * | 1/2015 | Swager | G01N 33/544 |
| | | | 436/85 |
| 2015/0053871 A1 * | 2/2015 | Grundfest | G01N 21/6408 |
| | | | 250/459.1 |
| 2015/0099650 A1 * | 4/2015 | Sood | G01N 33/533 |
| | | | 506/9 |
| 2015/0173621 A1 * | 6/2015 | Guo | G01J 3/2803 |
| | | | 250/362 |
| 2015/0182166 A1 * | 7/2015 | Evans | A61B 5/6833 |
| | | | 600/344 |
| 2015/0226743 A1 * | 8/2015 | Weiss | G01N 33/57407 |
| | | | 424/133.1 |
| 2015/0355118 A1 * | 12/2015 | Heissenstein | G01N 25/00 |
| | | | 250/340 |
| 2016/0067357 A1 * | 3/2016 | Francois | A61B 5/4848 |
| | | | 424/9.6 |
| 2017/0050046 A1 * | 2/2017 | Walder | A61N 5/062 |
| 2017/0370920 A1 | 12/2017 | Akama et al. | |
| 2018/0092177 A1 * | 3/2018 | Powers | H03K 5/08 |
| 2018/0172580 A1 * | 6/2018 | Bjorøy | G01J 3/10 |
| 2018/0209982 A1 | 7/2018 | Kabbarah et al. | |
| 2019/0008973 A1 * | 1/2019 | Eldor | A61K 47/44 |
| 2019/0249240 A1 * | 8/2019 | Rothberg | H01S 3/1115 |
| 2019/0271645 A1 * | 9/2019 | Xu | G01N 21/6454 |
| 2020/0249237 A1 * | 8/2020 | Deans | G01N 33/58 |
| 2020/0384126 A1 * | 12/2020 | Francois | A61B 5/4848 |
| 2021/0269711 A1 * | 9/2021 | Naumov | C01B 32/184 |

FOREIGN PATENT DOCUMENTS

| | | |
|---|---|---|
| JP | 2014-502728 A | 2/2014 |
| JP | 2018-517129 A | 6/2018 |
| WO | WO 2008/128352 A1 | 10/2008 |
| WO | WO 2012/092322 A1 | 7/2012 |
| WO | WO 2016/147825 A1 | 9/2016 |
| WO | WO 2016/172160 A1 | 10/2016 |
| WO | WO 2018/189370 A1 | 10/2018 |

* cited by examiner

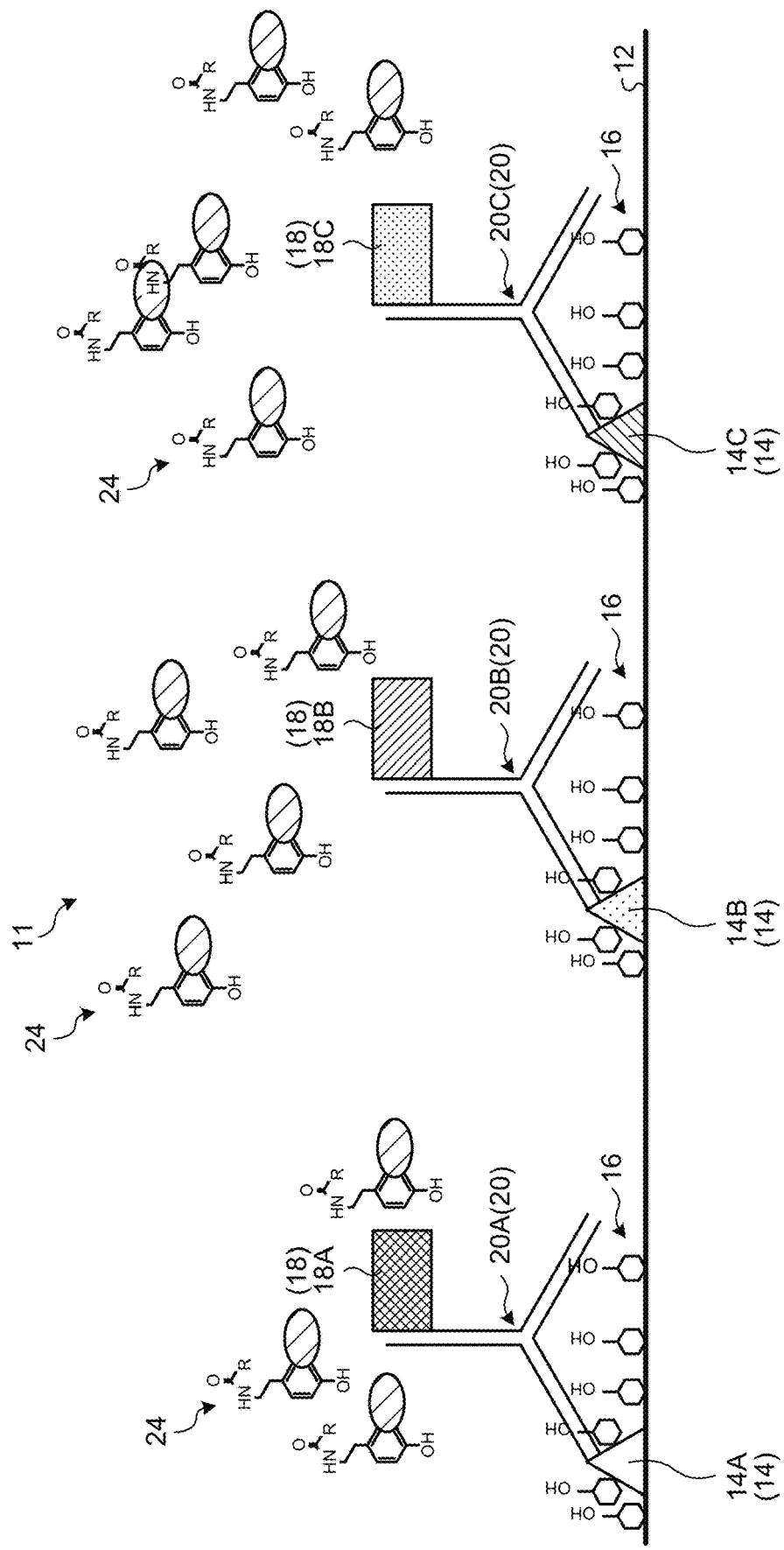

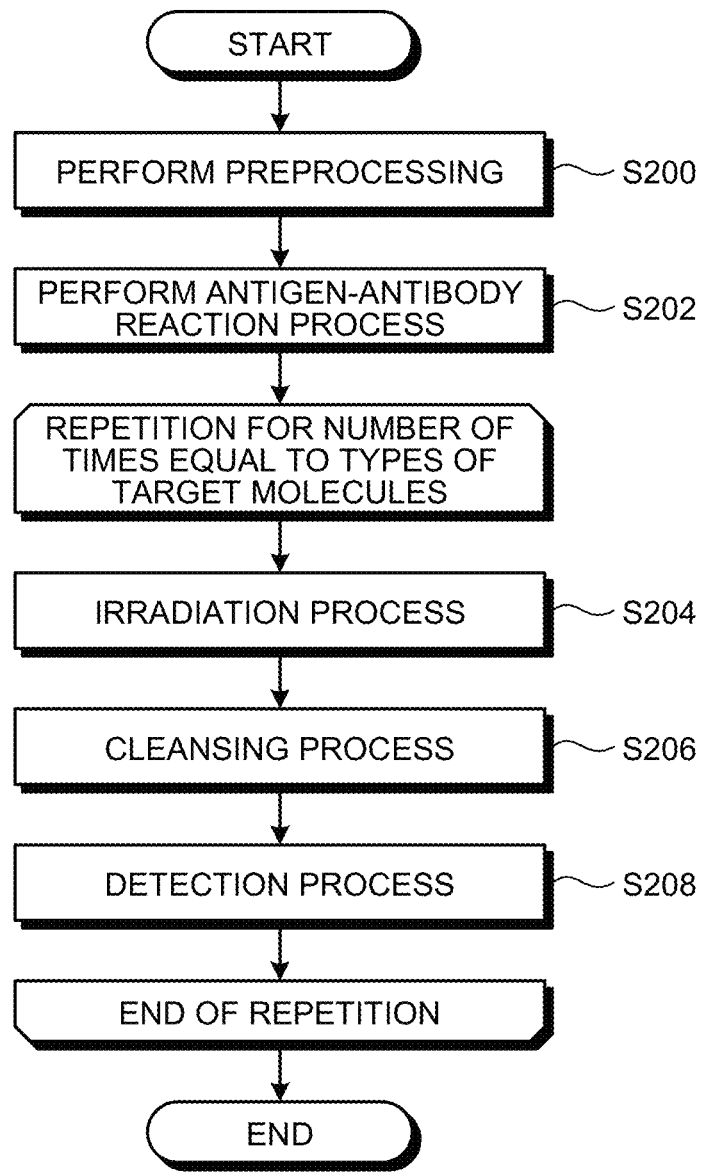

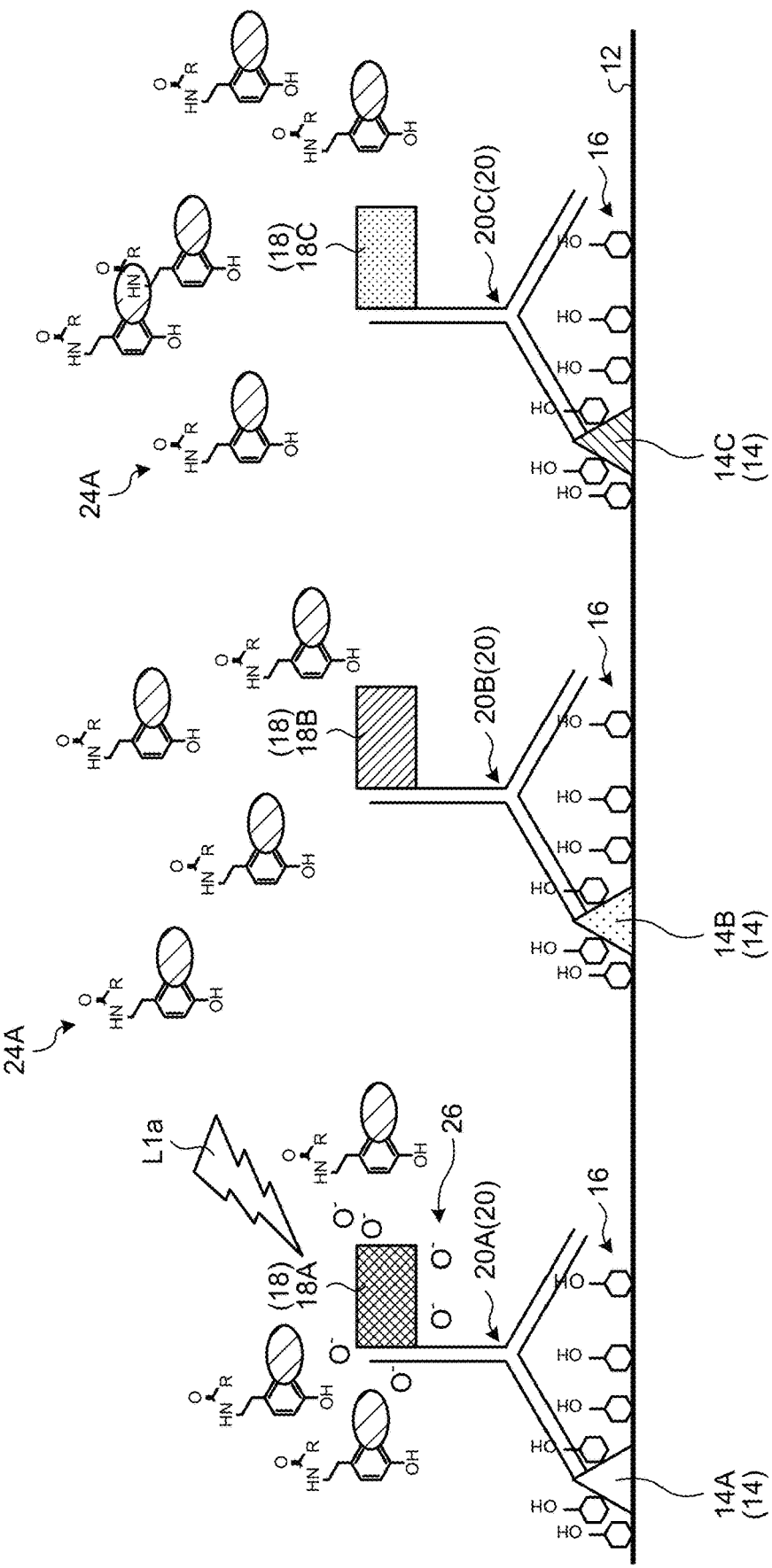

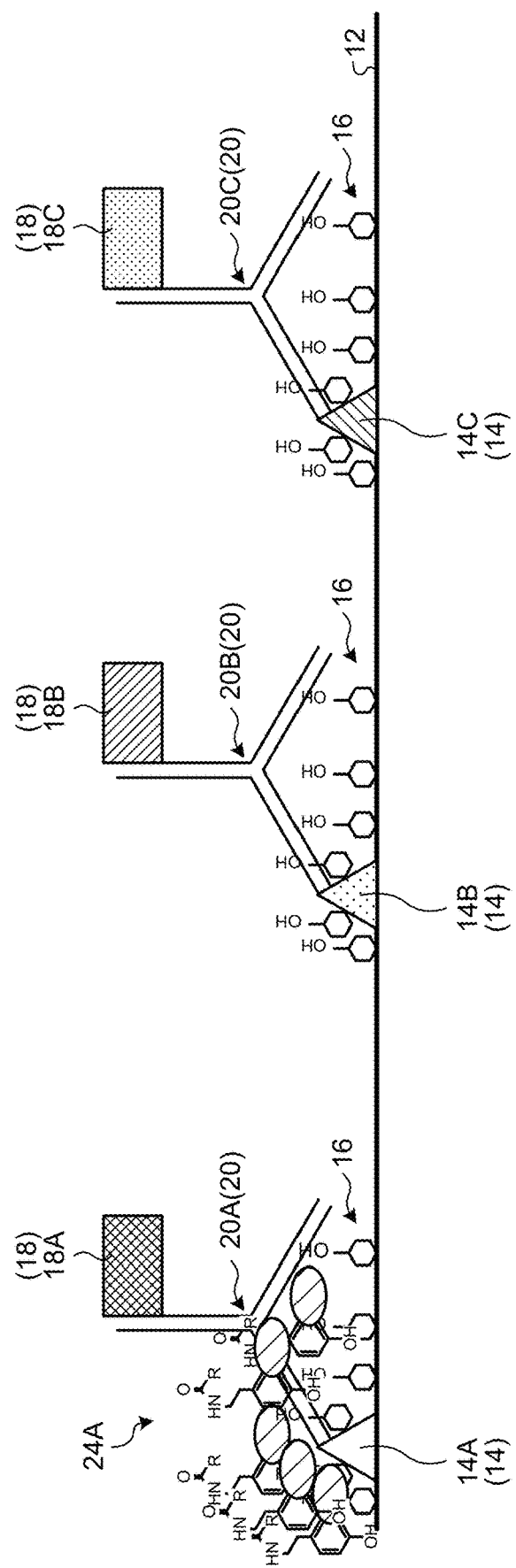

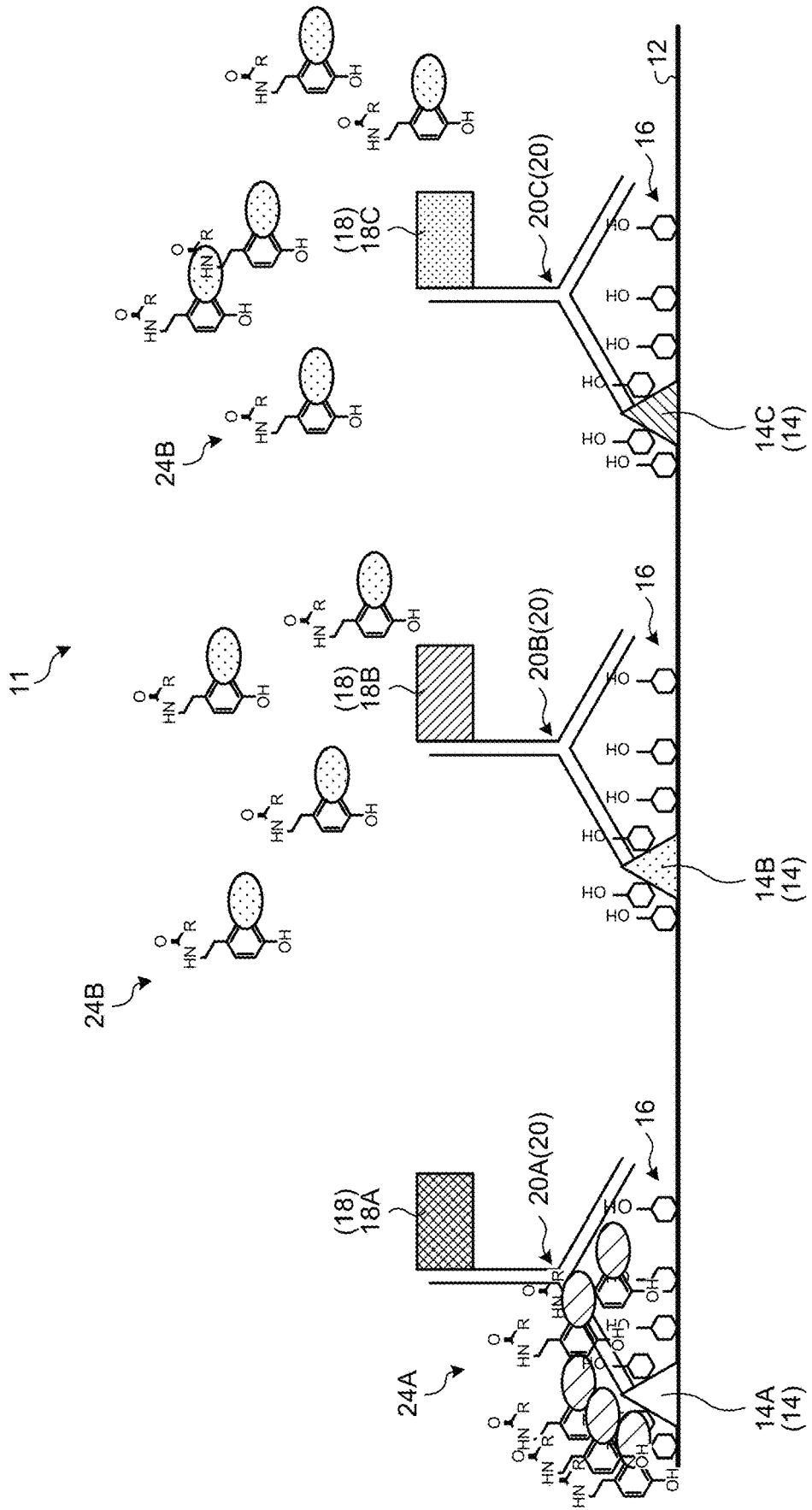

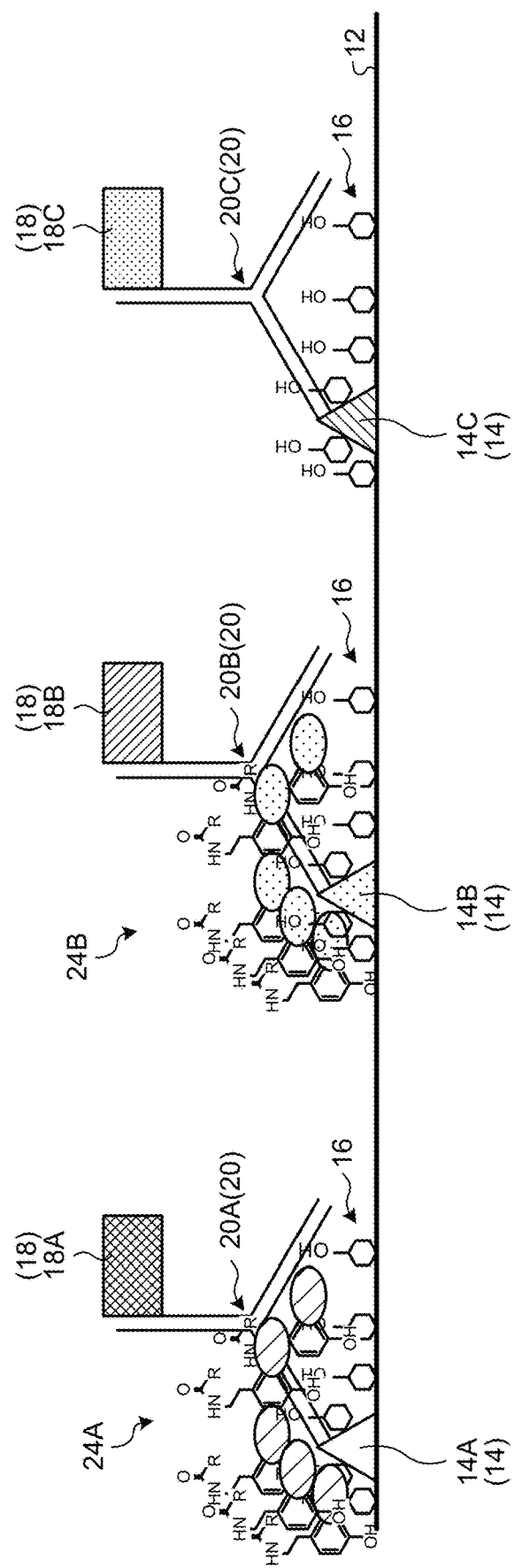

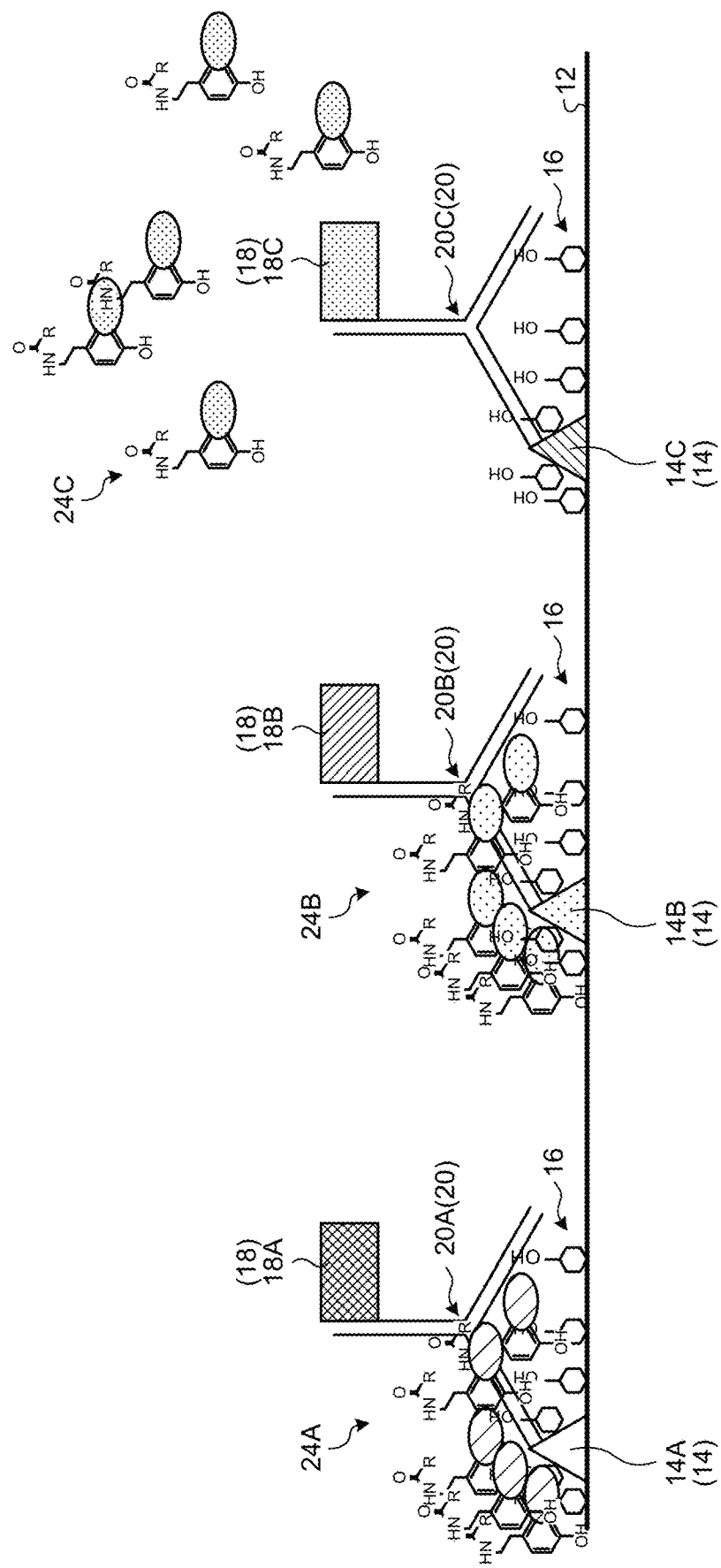

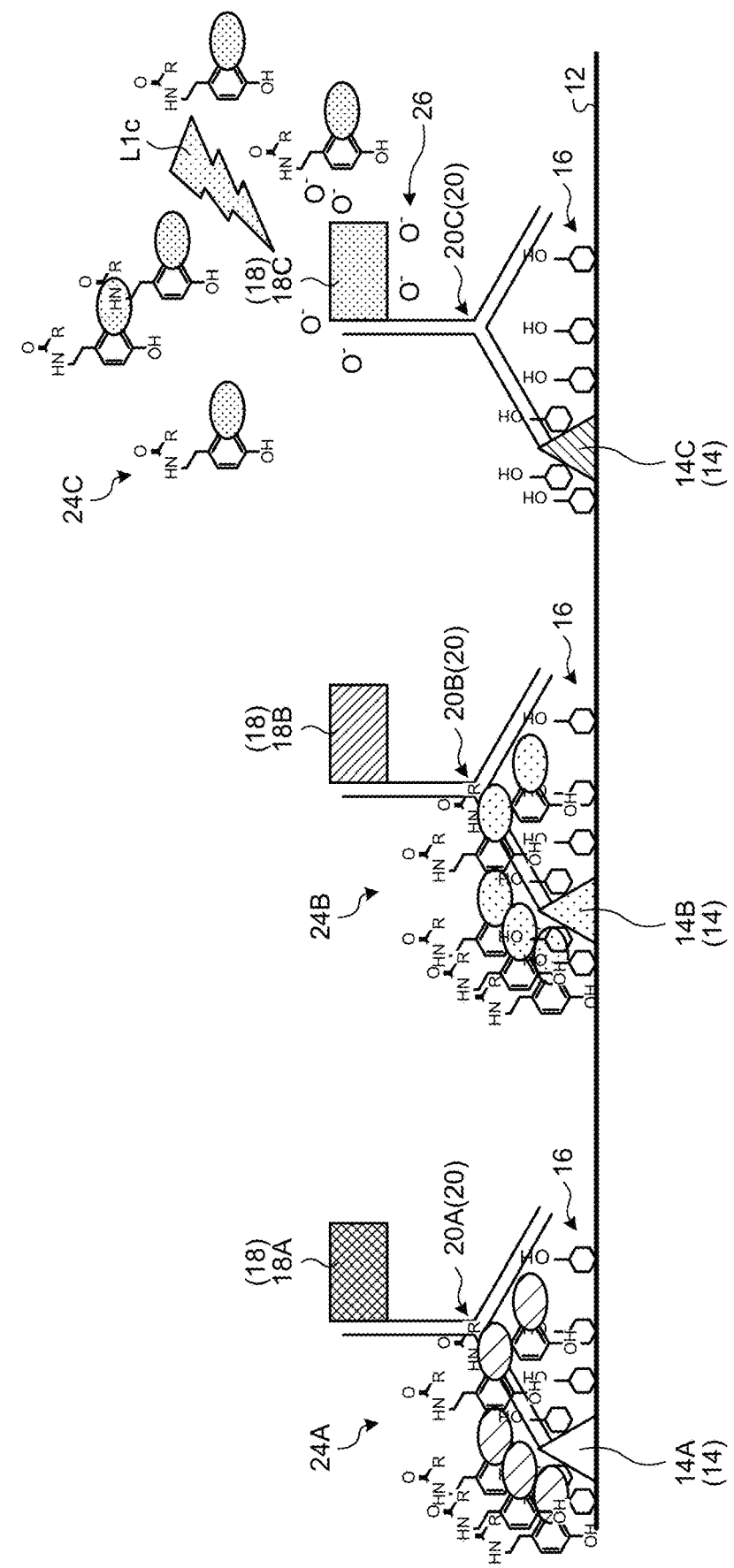

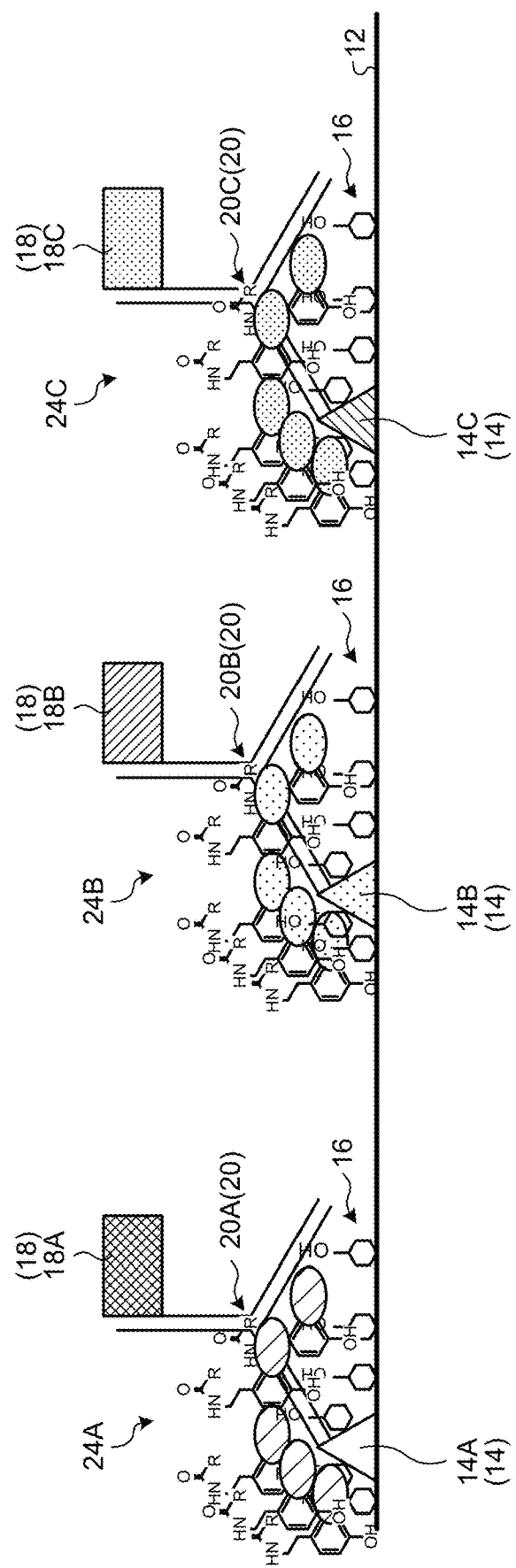

IMMUNOSTAINING METHOD, IMMUNOSTAINING SYSTEM, AND IMMUNOSTAINING KIT

CROSS-REFERENCE TO RELATED APPLICATIONS

This application claims the benefit under 35 U.S.C. § 371 as a U.S. National Stage Entry of International Application No. PCT/JP2019/041633, filed in the Japanese Patent Office as a Receiving Office on Oct. 24, 2019, which claims priority to Japanese Patent Application Number JP2018-205977, filed in the Japanese Patent Office on Oct. 31, 2018, each of which is hereby incorporated by reference in its entirety.

FIELD

The application concerned is related to an immunostaining method, an immunostaining system, and an immunostaining kit.

BACKGROUND

The immunostaining method is known as a method for detecting antigens in a sample with the use of antibodies. In order to achieve improvement in the detection sensitivity and the visibility in the immunostaining method, for example, a method is known in which biotin-labeled tyramide is applied to the principle of the CARD (Catalyced Reporter Deposition) technique (for example, refer to Patent Literature 1 to Patent Literature 5).

CITATION LIST

Patent Literature

Patent Literature 1: U.S. Pat. No. 5,731,158
Patent Literature 2: U.S. Pat. No. 5,583,001
Patent Literature 3: U.S. Pat. No. 5,196,306
Patent Literature 4: Japanese Laid-open Patent Publication No. H6-109734
Patent Literature 5: International Publication Pamphlet No. 2008/128352

SUMMARY

Technical Problem

However, in the conventional technology, after primary antibodies and secondary antibodies are sequentially made to react with the target antigens for measurement, an enzyme is added to the secondary antibodies and a radical is generated as a result of the enzymatic reaction attributed to the enzyme. For that reason, in the conventional technology, it becomes necessary to perform temperature adjustment according to the optimum temperature of the enzyme, adjustment of the reaction time according to the enzyme, and adjustment of a plurality of reaction solutions. Hence, performing immunostaining with ease is a difficult task.

In that regard, in the application concerned, an immunostaining method, an immunostaining system, and an immunostaining kit are proposed that enable performing immunostaining with ease.

Solution to Problem

To solve the above problem, an immunostaining method includes an irradiation process that includes irradiating, with a first excitation light, a specimen which includes a target molecule including electron donor, an antibody that is bound to the target molecule and that includes a generating agent for generating active species when irradiated with the first excitation light, and a pigment compound, and causing binding of the pigment compound and the electron donor due to active species generated from the generating agent when irradiated with the first excitation light.

BRIEF DESCRIPTION OF DRAWINGS

FIG. 5 is a schematic diagram illustrating an example of a specimen according to a second embodiment of the application concerned.

FIG. 6 is an explanatory diagram for explaining a sequence of processes performed in the immunostaining method according to the second embodiment of the application concerned.

FIG. 7B is an explanatory diagram for explaining irradiation with a first excitation light according to the second embodiment of the application concerned.

FIG. 7C is an explanatory diagram for explaining the state in which a pigment compound is bound to a target molecule according to the second embodiment of the application concerned.

FIG. 8A is a schematic diagram illustrating an example of the specimen according to the second embodiment of the application concerned.

FIG. 8C is an explanatory diagram for explaining the state in which a pigment compound is bound to a target molecule according to the second embodiment of the application concerned.

FIG. 9A is a schematic diagram illustrating an example of the specimen according to the second embodiment of the application concerned.

FIG. 9B is an explanatory diagram for explaining irradiation with a first excitation light according to the second embodiment of the application concerned.

FIG. 9C is an explanatory diagram for explaining the state in which a pigment compound is bound to a target molecule according to the second embodiment of the application concerned.

DESCRIPTION OF EMBODIMENTS

Embodiments of the application concerned are described below in detail.

First Embodiment

The immunostaining method according to a first embodiment includes an irradiation process. The irradiation process is a process in which a first excitation light is bombarded onto a specimen that includes a target molecule including an electron donor, an antibody that is bound to the target molecule and that includes a generating agent for generating active species when irradiated with the first excitation light, and a pigment compound; and in which the pigment compound and the electron donor are bound to each other due to the active species that are generated from the generating agent when irradiated with the first excitation light.

In the first embodiment, as a result of bombarding the first excitation light, the active species are generated from the generating agent included in the antibody. Due to the active species, the pigment compound binds to the electrical donors included in the target molecule. Thus, in the first embodiment, as a result of bombarding the first excitation light, it becomes possible to bind the pigment compound to the target molecule, and to amplify the signals in the vicinity of the target molecule. That is, in the immunostaining method according to the present embodiment, it is clear that immunostaining can be performed with ease as a result of the irradiation process in which the first excitation light is bombarded.

Meanwhile, the specimen that includes an antibody, which is bound to the target molecule including an electron donor and which includes a generating agent for generating active species when irradiated with the first excitation light, and includes a pigment compound can be provided as an immunostaining kit. In the immunostaining kit, due to the active species that are generated from the generating agent when irradiated with the first excitation light, there occurs binding of the electron donor and the pigment compound.

The detailed explanation is given below.

Figure 1A:
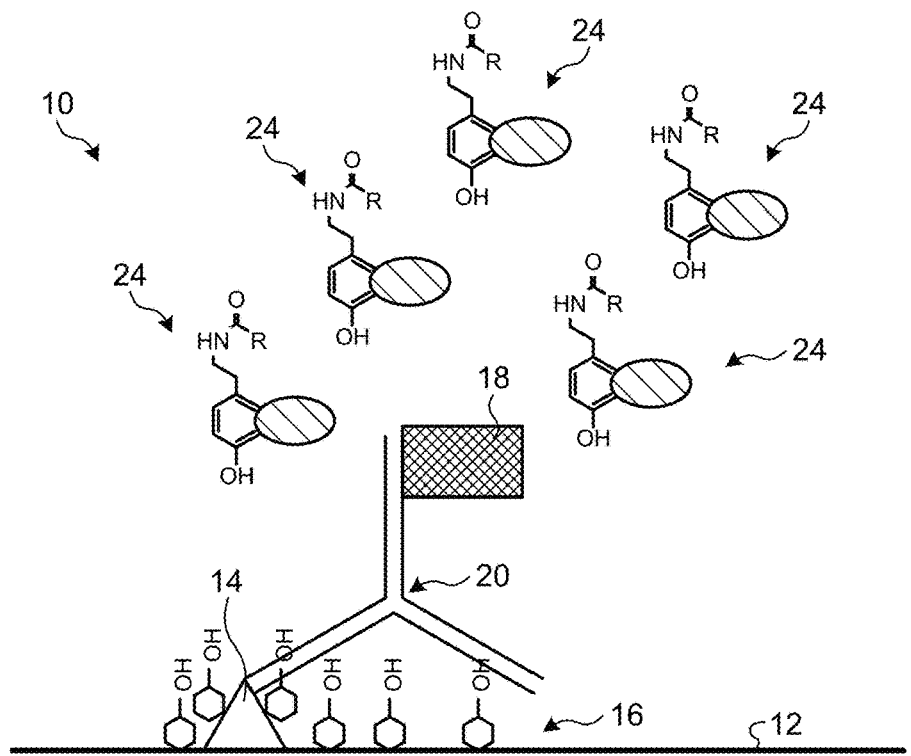
FIG. 1A is a schematic diagram illustrating an example of a specimen according to a first embodiment of the application concerned.

FIG. 1A is a schematic diagram illustrating an example of a specimen 10.

The specimen 10 includes a target molecule 14, an antibody 20, and a pigment compound 24.

[Target Molecule]

The target molecule 14 represents the immunostaining target. Examples of the target molecule 14 include protein (such as polypeptide or oligopeptide) and amino acid (including modified amino acid). Alternatively, the target molecule 14 can be a composite body of one or more of protein, amino acid, carbohydrate, lipid, and modified molecules thereof. Still alternatively, the target molecule 14 can be an antigen (a tumor marker, a signal transducer, a hormone, a growth regulatory agent for cancer, a metastasis regulatory agent, a growth regulatory agent, inflammatory cytokine, or a virus-related molecule) that is related to a disease to be subjected to pathological diagnosis. Still alternatively, the target molecule can be a metabolic product, DNA, RNA, micro RNA, polynucleotide, a toxin, a chemical drug, a virion, a cell, or hemoglobin. Meanwhile, the type of the target molecule 14 is not limited to the examples given herein.

In the specimen 10, it is desirable that the target molecule 14 is stabilized on a solid phase 12. The stabilization can be done using a known method such as physical adsorption. There is no particular restriction on the material and the shape of the solid phase 12. For example, as the solid phase 12, a microplate or a glass plate is used. Moreover, from the standpoint of signal detection, it is desirable that a transparent material is used as the solid phase 12.

[Electron Donor]

In the first embodiment, the target molecule 14 includes an electron donor 16.

The electron donor 16 is a chemical compound or a polar group having electron-donating capability. For example, the electron donor 16 is a chemical compound that can have a radical crosslinking reaction with the pigment compound 24 due to the active species generated as a result of irradiating the antibody 20 with the first excitation light. The active species represent radicals or free radicals.

For example, the electron donor 16 is an aromatic compound having a polar group. Examples of the polar group include the hydroxyl group, the methoxy group, the alkoxy group, the amino group, the methylamino group, the alkylamino group, the dialkylamino group, the trialkylamino group, and the methyl group. Meanwhile, alternatively, the electron donor 16 can be an aromatic compound not having a polar group.

The electron donor 16 can be selected according to the pigment compound 24 used in the specimen 10. For example, when the pigment compound 24 represents tyramide pigments, it is desirable that the electron donor 16 is an aromatic compound having the phenolic group. Examples of an aromatic compound having the phenolic group include protein or peptide having tyrosine residue.

In the first embodiment, the explanation is given for an example in which the electron donor 16 is protein having tyrosine residue. That is, in the first embodiment, the explanation is given for an example in which the target molecule 14 includes protein and has the composition including the electron donor 16.

Meanwhile, the electron donor 16 can also be stabilized on the solid phase 12. That is, in addition to being included in the target molecule 14, the electron donor 16 can also be stabilized on the solid phase 12.

[Antibody]

The antibody 20 has specificity against the target molecule 14. The antibody 20 can be appropriately selected according to the target molecule 14. For example, the antibody 20 is an antibody against an antigen (for example, HER2) that is related to a disease (such as a malignant tumor).

The antibody 20 can be a primary antibody or a secondary antibody. That is, the antibody 20 can be a primary antibody that binds to the target molecule 14 representing the antigen. Alternatively, the antibody 20 can be a secondary antibody that binds to the primary antibody which is bound to the antigen. Particularly, in a multistaining procedure (described later) in which a plurality of types of antibodies 20 is used, it is desirable that the antibodies 20 are primary antibodies so as to eliminate the need to take into account the interspecies crossover among the antibody host species. Meanwhile, if the antibody 20 is a secondary antibody, then the target molecule 14 can be a primary antibody bound to the antigen that has specificity against the antibody 20. In the first embodiment, the explanation is given for an example in which the antibody 20 is a primary antibody.

[Generating Agent]

The antibody 20 includes a generating agent 18.

The generating agent 18 is a substance that generates active species when irradiated with the first excitation light. In other words, the generating agent 18 is a substance that becomes excited when irradiated with the light having a particular wavelength range, and thus generates active species. In order to hold down the generation of active species from the pigment compound and in order to attain multi-staining capability, it is desirable that the excitation spectrum of the generating agent 18 has a longer wavelength than the excitation spectrum of the pigment compound 24 (described later).

Examples of the generating agent 18 include cyanine pigments such as Cy3, Cy5, and Cy7; fluorescein derivatives such as fluorescein isothiocyanate (FITC); coumarine dye; methylene blue; rose bengal; Fenton's reagent; and fluorescent protein such as green fluorescent protein (GFP). From among those examples, it is desirable to use Cy5 as the generating agent 18 for the reason of having a long wavelength in the visible frequency range and having a proven record of active species generation. Meanwhile, as long as the generating agent 18 is a substance that generates active species when irradiated with the first excitation light, it is not limited to pigments such as cyanine pigments mentioned above.

The generating agent 18 can be bound to the antibody 20 using a known method.

[First Excitation Light]

As long as the first excitation light is a light having the wavelength range causing generation of the active species from the generating agent 18, it serves the purpose. The wavelength range of the first excitation light can be appropriately adjusted according to the generating agent 18 representing the irradiation target.

Meanwhile, in order to ensure that the bombardment of the first excitation light results in the generation of active species only from the generating agent 18, it is desirable that the substances other than the generating agent 18 in the specimen 10 correspond to the light of wavelength ranges that does not cause generation of active species. More particularly, it is desirable to have the first excitation light of such a wavelength range that the generating agent 18 generates active species but the pigment compound 24 does not generate active species.

[Pigment Compound]

The pigment compound 24 is a substance labeled with pigments. For example, the pigment compound 24 is an aromatic compound labeled with pigments.

As long as the pigments included in the pigment compound 24 are a substance with which the pigment compound 24 can be labeled, it serves the purpose. Examples of the pigments include Rhodamine Green, Alexa488, GFP (green fluorescent protein), YOYO1 (dimer of oxazole yellow), TAMRA (carboxytetramethylrhodamine), TMR (methylrhodamine), EVOblue™, and Alexa647. However, the pigments included in the pigment compound 24 are not limited to these examples.

Thus, as long as the pigment compound 24 is a substance labeled with the abovementioned pigments, it serves the purpose. The labeling can be performed using a known method. Moreover, particularly, it is desirable that the pigment compound 24 reacts with the electron donor and initiates a crosslinking reaction, or reacts with the electron donor and forms an insoluble compound.

In the pigment compound 24, the compound portion other than the pigments is, more particularly, tyramide pigments (pigment-labeled tyramide), DAB (3,3'-diaminobenzidine tetra-hydrochloride), arylazide, or glycyl tyrosine. From among them, it is desirable that the pigment compound 24 includes tyramide pigments for having a high reactivity with active oxygen and for causing a crosslinking reaction with tyrosine.

The pigment compound 24 can be procured also as a commercial item. Specific examples of the commercial items for the pigment compound 24 can include the following.

Molecular Probes: Alexa Fluor 350, Alexa Fluor 488, Alexa Fluor 532, Alexa Fluor 546, Alexa Fluor 568, Alexa Fluor 594, and Alexa Fluor 647.

Perkin-Elmer Corporation: NEL741 TSA Plus Fluorescein System, NEL742 TSA Plus TMR System, NEL744 TSA Plus Cyanine 3 System, NEL745 TSA Plus Cyanine 5 System Meanwhile, from the standpoint of easily detecting the pigment compound 24 that is bound to the target molecule 14, it is desirable that the pigment compound 24 is made to become excited and produce luminescence, such as fluorescence, when irradiated with a second excitation light. Thus, as the pigment compound 24, a substance satisfying the abovementioned conditions can be selected.

As long as the second excitation light is a light having a wavelength range that causes excitation of the pigment compound 24, it serves the purpose. Herein, it is desirable that the first excitation light, which is bombarded for causing generation of active species from the generating agent 18 of the antibody 20, has a different wavelength range than the wavelength range of the second excitation light, which causes excitation of the pigment compound 24. That is, it is desirable that the first excitation light and the second excitation light have different wavelength ranges.

Moreover, it is desirable that the second excitation light has a shorter wavelength range than the wavelength range of the first excitation light. In other words, it is desirable that the first excitation light has a longer wavelength range than the wavelength range of the second excitation light.

[Immunostaining Method]

Given below is the specific explanation of the immunostaining method according to the first embodiment.

The immunostaining method according to the first embodiment includes preprocessing, an antigen-antibody reaction process, an irradiation process, a cleansing process, and a detection process. Thus, in the immunostaining method according to the first embodiment; the preprocessing, the antigen-antibody reaction process, the irradiation process, the cleansing process, and the detection process are performed in that order.

Given below is the detailed explanation of each process.

[Preprocessing]

Firstly, the preprocessing is performed. The preprocessing includes a stabilization process, an activation process, and a blocking process.

The stabilization process is a process for stabilizing the target molecule 14, which includes the electron donor 16, on the solid phase 12. Herein, the stabilization can be performed using a known method. Alternatively, the solid phase 12 having the target molecule 14 stabilized thereon can be kept ready.

The activation process is a process for activating the target molecule 14. Herein, activation can be performed using a known method. Moreover, regarding the activation conditions, a known method can be used according to the type of the target molecule 14.

The blocking process is a process for blocking the solid phase 12 using a blocking agent. As the blocking agent, a known substance can be used. Examples of the blocking agent include protein materials such as bovine serum albumin, casein, and skimmed milk. Alternatively, it is also possible to use a commercially available blocking agent.

[Antigen-Antibody Reaction Process]

In the antigen-antibody reaction process, the antibody 20 including the generating agent 18 is bound to the target molecule 14 due to the antigen-antibody reaction. The antigen-antibody reaction process includes the antigen-antibody reaction used in the standard immunostaining such as the primary antibody method or the secondary antibody method. The conditions in the antigen-antibody reaction can be adjusted according to the type of the target molecule 14 and the type of the antibody 20.

[Irradiation Process]

In the irradiation process, firstly, the antibody 20, which includes the generating agent 18 but which is not involved in the antigen-antibody reaction, is removed by cleansing.

Then, the pigment compound 24 is added. The type of the pigment compound 24 to be added can be adjusted according to the type of the generating agent 18 included in the antibody 20 that is already bound to the target molecule 14.

For example, in the case of using rose Bengal as the generating agent 18, it is desirable to use tyramide pigments (Alexa 647 coupled to tyramine) as the pigment compound 24.

Alternatively, for example, in the case of using Cy5 as the generating agent 18, it is desirable to use tyramide pigments (Cy3 coupled to tyramine) as the pigment compound 24.

Still alternatively, for example, in the case of using FITC as the generating agent 18, it is desirable to use tyramide pigments (Alexa Fluor 350 to tyramine) as the pigment compound 24.

Still alternatively, for example, in the case of using GFP as the generating agent 18, it is desirable to use tyramide pigments (amino coumarine acid) as the pigment compound 24.

If any of the abovementioned combinations is used as the combination of the generating agent 18 and the pigment compound 24, multistaining becomes easier to perform as compared to the case of not using any combination.

To one molecule of the antibody 20 included in the specimen 10, it is desirable to add five or more and six or less molecules of the pigment compound 24. The additive amount of the pigment compound 24 can be appropriately adjusted according to the type of the pigment compound 24 and the type of the antibody 20, and is not limited to the range mentioned above.

Subsequently, the specimen 10, which is manufactured by performing the processes explained above and which includes the target molecule 14, the antibody 20, and the pigment compound 24, is irradiated with the first excitation light.

Figure 1B:
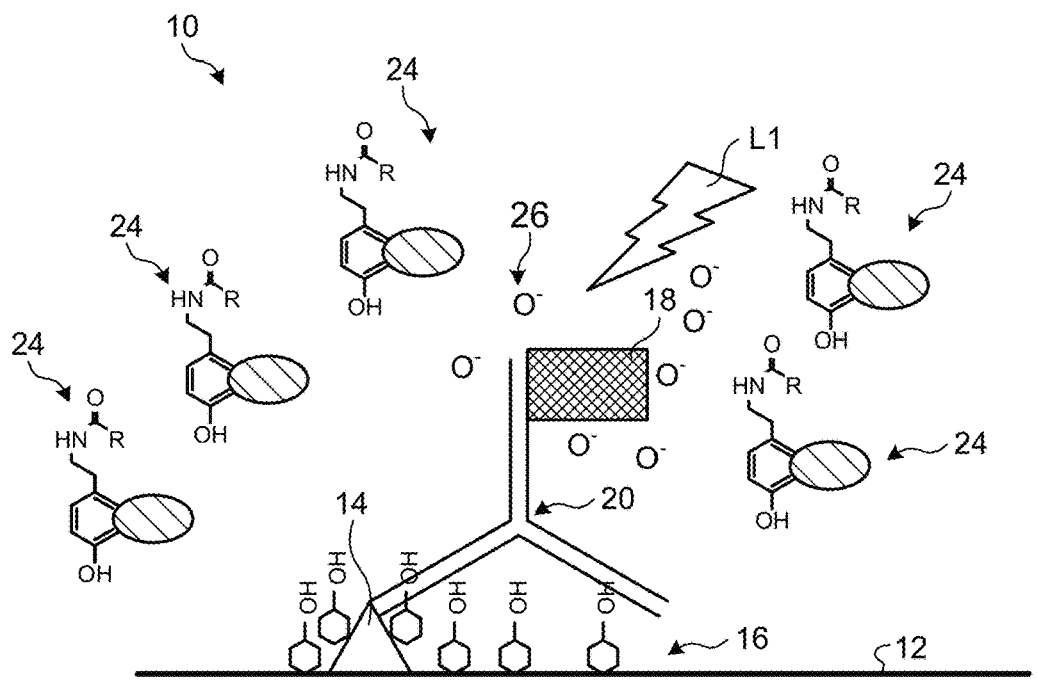
FIG. 1B is an explanatory diagram for explaining irradiation with a first excitation light according to the first embodiment of the application concerned.

FIG. 1B is an explanatory diagram for explaining the irradiation of the specimen 10 with a first excitation light L1.

As described earlier, the first excitation light L1 is a light having such a wavelength range that the generating agent 18 included in the antibody 20 generates active species 26. Thus, when irradiated with the first excitation light L1, the generating agent 18 generates the active species 26.

Due to the action of the active species 26, the pigment compound 24 undergoes a radical crosslinking reaction with the electron donor 16 having abundant electrons, and gets bound to the target molecule 14 including the electron donor 16 or forms an insoluble substance.

Figure 1C:
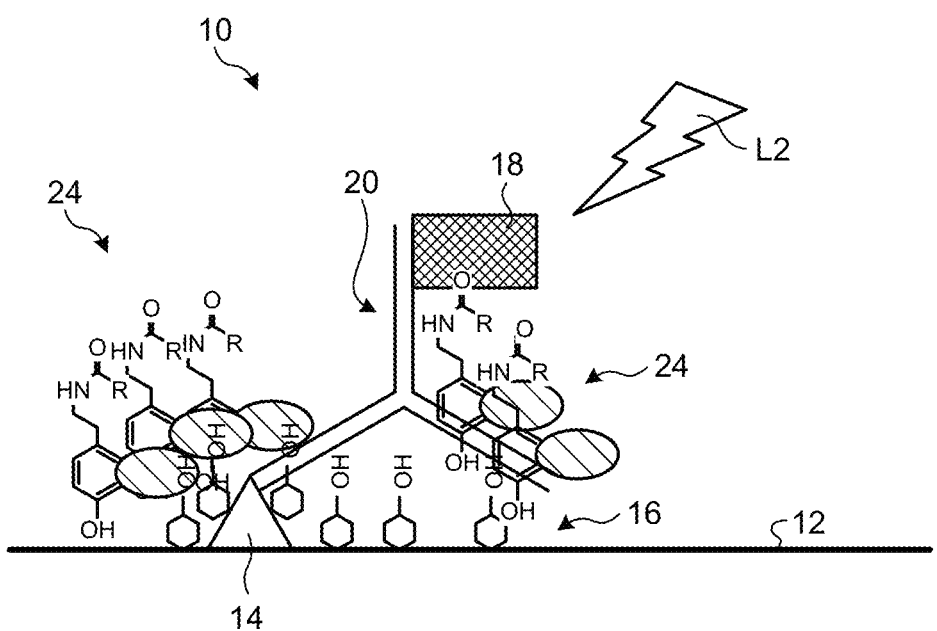
FIG. 1C is a schematic diagram illustrating the state in which a pigment compound is bound to a target molecule according to the first embodiment of the application concerned.

FIG. 1C is a schematic diagram illustrating the state in which the pigment compound 24 is bound to the target molecule 14. The active species 26 that are generated as a result of irradiation with the first excitation light L1 have a short life-span (singlet oxygen 2 µs, hydroxyl radical 200 µs) and do not diffuse. Hence, the active species 26 are generated only in the vicinity of the target molecule 14. During the irradiation with the first excitation light L1, the active species 26 are repeatedly generated from the generating agent 18. That enables signal amplification in the vicinity of the target molecule 14. Moreover, since the active species 26 are generated only during the irradiation with the first excitation light L1, it is easier to control the amplification factor unlike in the enzymatic reaction.

[Cleansing Process]

The cleansing process is a process for cleansing the target molecule 14 to which the pigment compound 24 is bound. As a result of performing the cleansing process, the unreacted pigment compound 24 is removed from the specimen 10. The cleansing can be performed using a buffered solution such as PBS (Phosphate Buffered Saline). For example, a method can be implemented in which the target molecule 14, to which the pigment compound 24 is bound, is immersed for a predetermined period of time in the PBS adjusted to the room temperature (1° C. to 30° C.). Moreover, while the target molecule 14 is immersed, the PBS can be changed.

[Detection Process]

In the specimen 10, the target molecule 14 is detected by measuring or observing the color of the pigment compound 24 that is bound to the target molecule 14.

The color of the pigment compound 24, which is bound to the target molecule 14, can be measured using optical diffraction, absorbance, fluorescence, Raman scattering, phosphorescence, light emission, radioactivity, or SPR (surface plasmon resonance).

The color of the pigment compound 24, which is bound to the target molecule 14, can be measured using a known device. For example, a spectrophotometer or an imaging device that captures images is used for the measurement. Alternatively, the color of the pigment compound 24 can be observed using a light microscope, or a fluorescence microscope, or a confocal microscope; and the target molecule 14 can be detected.

More particularly, the specimen 10, which has been subjected to the irradiation process and the cleansing process (see FIG. 1C), is irradiated with a second excitation light L2. At that time, irradiation with the second excitation light L2 can be performed using an excitation light source and an optical filter that correspond to the absorption maximum wavelength and the excitation spectrum of the pigment compound 24. Then, the detection result regarding the light emitted as a result of excitation of the pigment compound 24 due to the irradiation with the second excitation light L2 can be obtained using an imaging device. Subsequently, the number of luminescent spots or the light emission luminescence can be measured using a known method, and the target molecule 14 can be detected (that is, quantitated).

[Immunostaining System]

Given below is the explanation of an example of the immunostaining system meant for implementing the immunostaining method explained above.

Figure 2:
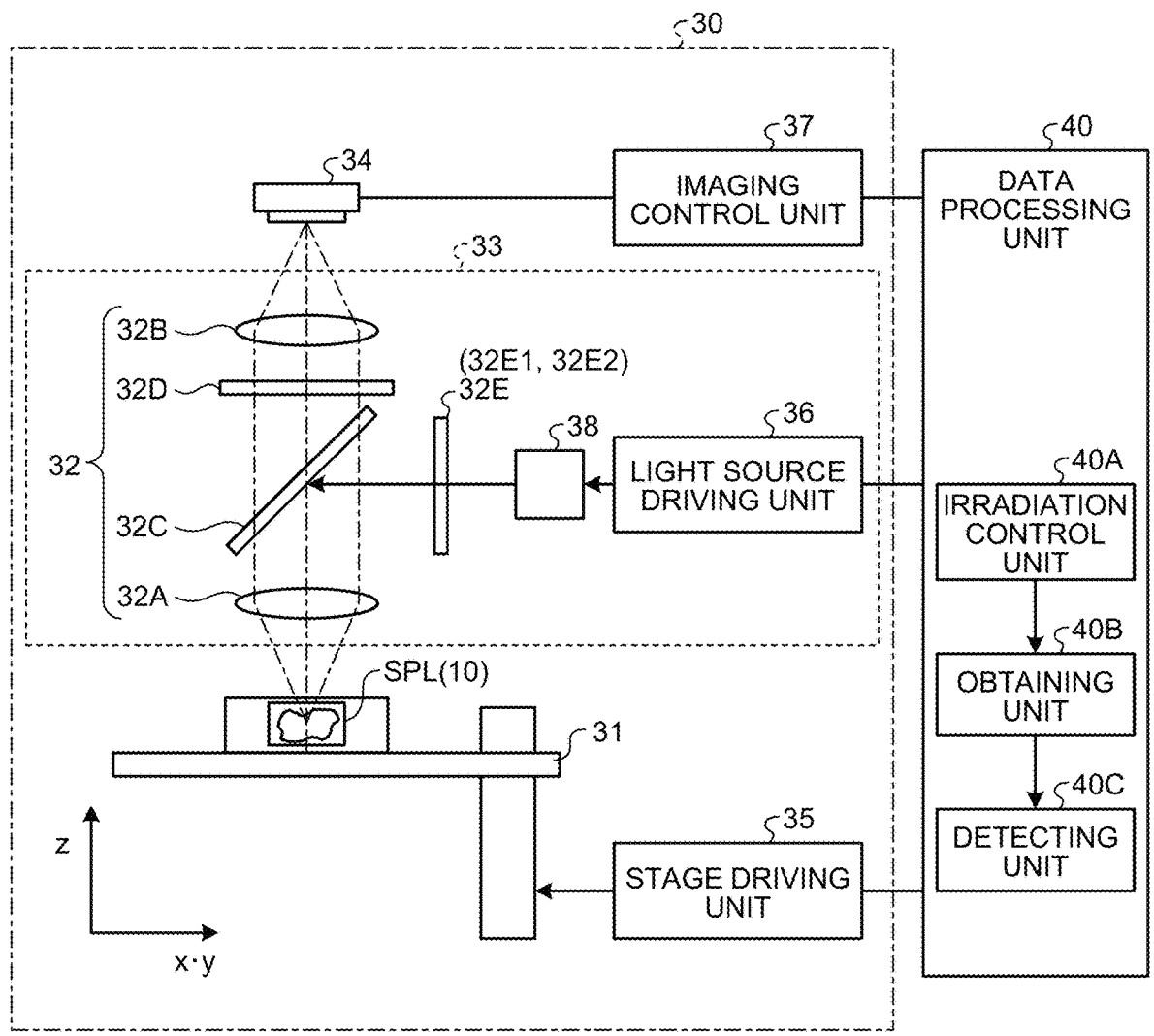
FIG. 2 is a schematic diagram illustrating an example of an immunostaining system according to the first embodiment of the application concerned.

FIG. 2 is a schematic diagram illustrating an example of an immunostaining system 1. The immunostaining system 1 includes a microscope 30 and a data processing unit 40.

The microscope 30 includes a stage 31, an irradiating unit 33, and an imaging device 34. The stage 31 has a placement surface on which a sample SPL representing the specimen 10 can be placed. The stage 31 is configured to be able to move in the horizontal direction (the x-y planar direction) and the vertical direction (the z-axis direction) under the control of a stage driving unit 35.

The irradiating unit 33 irradiates the specimen 10 with the first excitation light L1 or the second excitation light L2. The irradiating unit 33 includes an optical system 32, a light source driving unit 36, and a light source 38.

The optical system 32 is disposed above the stage 31. The optical system 32 includes an objective lens 32A, an imaging lens 32B, a dichroic mirror 32C, an emission filter 32D, and excitation filters 32E. Examples of the light source 38 include an electrical light bulb such as a mercury lamp, and an LED (Light Emitting Diode).

The excitation filters 32E are filters that, of the light emitted from the light source 38, selectively transmit the light having the wavelength range of the first excitation light L1 and the wavelength range of the second excitation light L2. In the microscope 30, a plurality of excitation filters 32E having different transmittable wavelength ranges is installed. More particularly, in the microscope 30, an excitation filter 32E1 is installed that selectively transmits the light having the wavelength range of the first excitation light L1, and an excitation filter 32E2 is installed that selectively transmits the light having the wavelength range of the second excitation light L2.

The dichroic mirror 32C guides, to the objective lens 32A, the light that was emitted from the light source 38 and that has passed through the excitation filters 32E. The objective lens 32A focuses that light onto the sample SPL. Then, the objective lens 32A and the imaging lens 32B form, onto the imaging surface of the imaging device 34, a magnified image obtained by magnifying the image of the sample SPL by a predetermined magnifying power.

The light source driving unit 36 controls the light source 38 and controls the switching between the excitation filter 32E1 and the excitation filter 32E.

For example, the light source driving unit 36 controls the position of the excitation filter 32E1 in such a way that the light emitted from the light source 38 passes through the excitation filter 32E1, so that the sample SPL representing the specimen 10 gets irradiated with the first excitation light L1. Similarly, the light source driving unit 36 controls the position of the excitation filter 32E2 in such a way that the light emitted from the light source 38 passes through the excitation filter 32E2, so that the sample SPL representing the specimen 10 gets irradiated with the second excitation light L2.

The imaging device 34 obtains a captured image of the specimen 10. In the imaging device 34, a magnified image of the specimen 10 is formed via the objective lens 32A and the imaging lens 32B. As a result of the image formation, the imaging device 34 obtains a captured image in which the specimen 10 is magnified.

The imaging device 34 includes a photoelectric conversion element and represents an imager for obtaining images from the incident light. Examples of the imaging device 34 include a CCD (Charge Coupled Device) and a CMOS (Complementary Metal Oxide Semiconductor) image sensor. Meanwhile, the imaging lens 32B and the emission filter 32D can be changed to spectroscopic elements. In that case, either a spectroscopic camera is used that implements the run-scan method representing a spatial scanning method, or a two-dimensional spectroscopic camera is used that implements a temporal scanning method.

The imaging device 34 obtains a captured image by capturing the specimen 10 under the control of an imaging control unit 37, and outputs the captured image to the data processing unit 40.

The data processing unit 40 includes an irradiation control unit 40A, an obtaining unit 40B, and a detecting unit 40C. Herein, for example, some or all of the irradiation control unit 40A, the obtaining unit 40B, and the detecting unit 40C can be implemented by making a processor such as a CPU execute programs, that is, can be implemented using software; or can be implemented using hardware such as an IC (Integrated Circuit); or can be implemented using a combination of software and hardware.

The irradiation control unit 40A controls the irradiating unit 33.

More specifically, after the preprocessing is over but before the irradiation process is performed, when the sample SPL representing the specimen 10 is placed on the stage 31, the irradiation control unit 40A controls the light source driving unit 36 to irradiate the specimen 10 with the first excitation light L1. Regarding the input of the information indicating that the specimen 10 prior to being subjected to the irradiation process is placed on the stage 31, the irradiation control unit 40A can receive an operation instruction from the user. Under the control of the irradiation control unit 40A, the light source driving unit 36 controls the position of the excitation filter 32E1 in such a way that the light which would be emitted from the light source 38 would pass through the excitation filter 32E1, and then makes the light source 38 emit the light.

As a result, the specimen 10 that has been subjected to the preprocessing gets irradiated with the first excitation light L1. As explained earlier, as a result of the irradiation with the first excitation light L1, the active species 26 are generated from the generating agent 18, and the pigment compound 24 binds to the target molecule 14 due to the active species 26 (see FIGS. 1B and 1C).

Subsequently, the irradiation control unit 40A controls the light source driving unit 36 in such a way that the specimen 10 that has been subjected to the irradiation process is irradiated with the second excitation light L2. Herein, it is desirable that the irradiation control unit 40A performs control in such a way that the second excitation light L2 is bombarded onto the specimen 10 that has been subjected to the irradiation process, in which the first excitation light L1 is bombarded, and that has been subjected to the cleansing process. For example, regarding the input of the information indicating that the irradiation process and the cleansing process are over, the irradiation control unit 40A can receive an operation instruction from the user.

Under the control of the irradiation control unit 40A, the light source driving unit 36 controls the position of the excitation filter 32E2 in such a way that the light which would be emitted from the light source 38 would pass through the excitation filter 32E2, and then makes the light source 38 emit the light.

As a result, the specimen 10 that has been subjected to the irradiation process and the cleansing process gets irradiated with the second excitation light L2. As a result of the irradiation with the second excitation light L2, the pigment compound 24 that is bound to the target molecule 14 becomes excited and produces luminescence.

The obtaining unit 40B obtains the captured image of the specimen 10. More specifically, while the specimen 10 is being irradiated with the second excitation light L2, the obtaining unit 40B controls the imaging control unit 37 to obtain a captured image of the specimen 10, and thus obtains the captured image of the specimen 10.

Based on the captured image obtained by the obtaining unit 40B, the detecting unit 40C detects the pigment compound 24 that is bound to the electron donor 16 of the target molecule 14. For example, the detecting unit 40C analyzes the captured image according to a known image processing method; measures the number of luminescent spots or the light emission luminescence using a known method; and detects (i.e., quantitates) the target molecule 14.

Meanwhile, the detecting unit 40C can also output the detection result regarding detecting the target molecule 14. For example, the data processing unit 40 is configured to be electrically connected to an output unit such as a display device, a communication device, or a sound output device. Thus, the detecting unit 40C can output the detection result regarding detecting the target molecule 14 to the output unit.

Given below is the explanation of a hardware configuration of the data processing unit 40.

Figure 3:
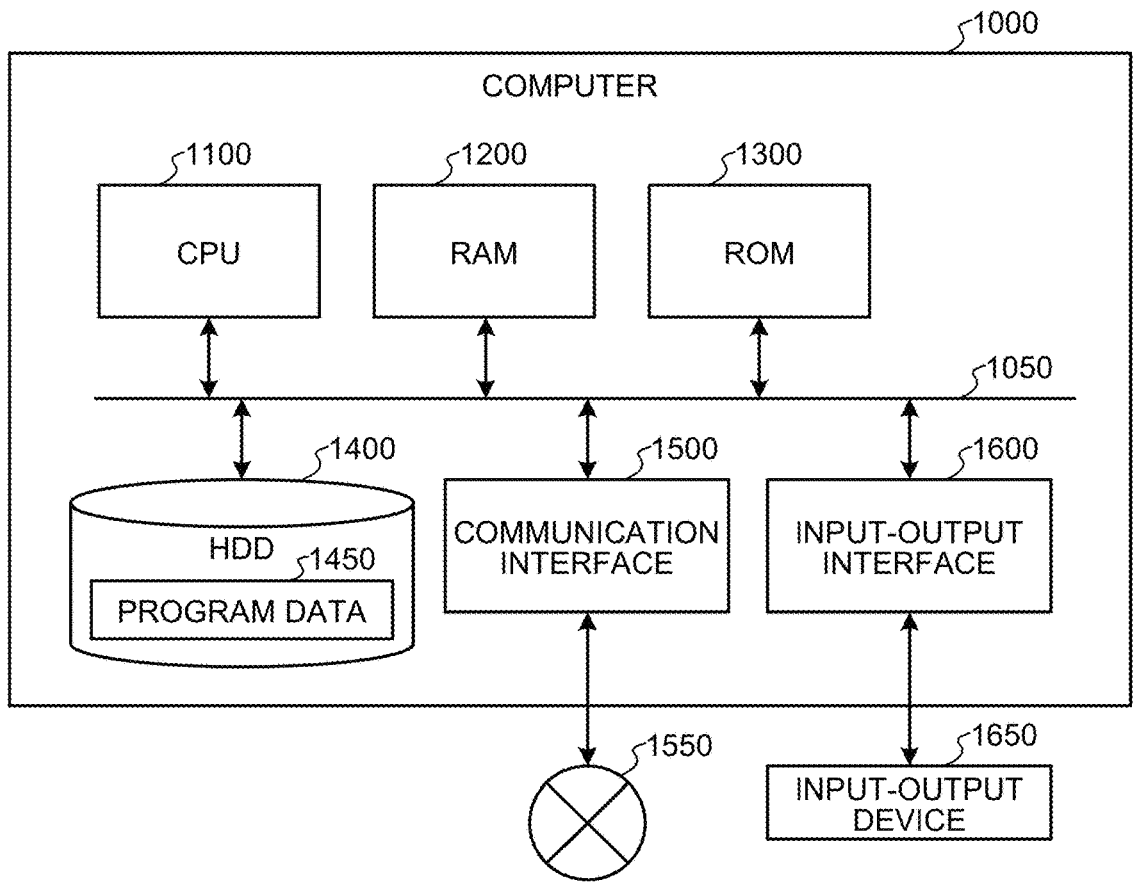
FIG. 3 is a hardware configuration diagram illustrating an example of a computer that implements the functions of a data processing unit according to the first embodiment of the application concerned.

FIG. 3 is a hardware configuration diagram illustrating an example of a computer 1000 that implements the functions of the data processing unit 40.

The computer 1000 includes a CPU 1100, a RAM 1200, a ROM (Read Only Memory) 1300, an HDD (Hard Disk Drive) 1400, a communication interface 1500, and an input-output interface 1600. Moreover, these constituent elements of the computer 1000 are connected to each other by a bus 1050.

The CPU 1100 operates based on programs stored in the ROM 1300 or the HDD 1400, and controls the other constituent elements. For example, the CPU 1100 loads the programs from the ROM 1300 or the HDD 1400 into the RAM 1200, and performs operations according to the programs.

The ROM 1300 is used to store a boot program such as the BIOS (Basic Input Output System) that is executed by the CPU 1100 at the time of booting of the computer 1000, and to store programs dependent on the hardware of the computer 1000.

The HDD 1400 is a computer-readable recording medium used to non-temporarily record the programs executed by the CPU 1100 and the data used in the programs. More particularly, the HDD 1400 is a recording medium used to record a program according to the application concerned, which represents an example of program data 1450.

The communication interface 1500 is an interface for connecting the computer 1000 to an external network 1550 (for example, the Internet). For example, via the communication interface 1500, the CPU 1100 receives data from other devices or sends data generated therein to other devices.

The input-output interface 1600 is an interface for connecting the computer 1000 to an input-output device 1650. For example, via the input-output interface 1600, the CPU 1100 communicates with the input-output device 1650 of each of the imaging control unit 37, the light source driving unit 36, and the stage driving unit 35. Moreover, the input-output interface 1600 can also function as a media interface for reading programs recorded in predetermined recording mediums (media). Examples of the media include an optical recording medium such as a DVD (Digital Versatile Disc) or a PD (Phase change rewritable Disk); a magneto-optical recording medium such as an MO (Magneto-Optical disk); a tape medium; a magnetic recording medium; and a semiconductor memory.

For example, when the computer 1000 functions as the data processing unit 40, the CPU 1100 of the computer 1000 executes an information processing program loaded in the RAM 1200 and implements functions such as the irradiation control unit 40A. Meanwhile, the HDD 1400 is used to store the data of the information processing program according to the application concerned. The CPU 1100 can read the program data 1450 from the HDD 1400 and execute it, or can obtain the program from some other device via the external network 1550.

Given below is the explanation of an exemplary sequence of information processing performed in the immunostaining system 1.

Figure 4:
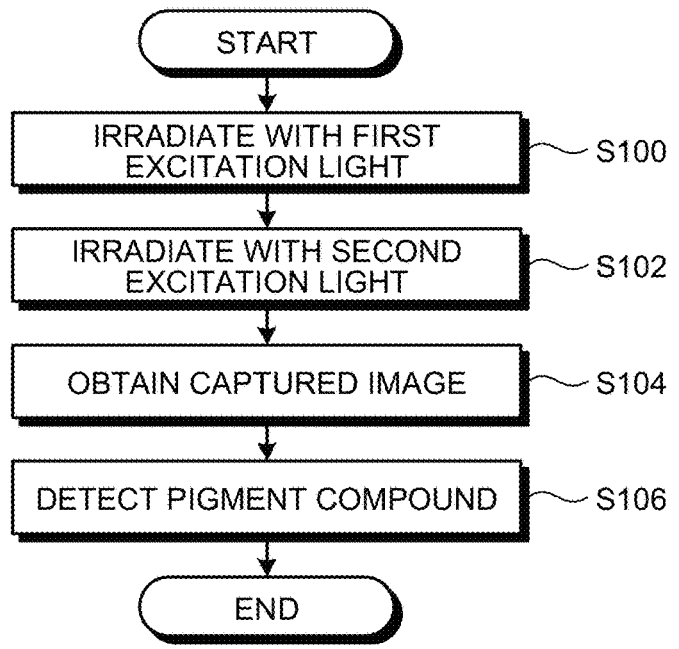
FIG. 4 is a flowchart for explaining an exemplary sequence of information processing performed in the immunostaining system according to the first embodiment of the application concerned.

FIG. 4 is a flowchart for explaining an exemplary sequence of information processing performed in the immunostaining system 1.

Firstly, after the preprocessing is over but before the irradiation process is performed, when the sample SPL representing the specimen 10 is placed on the stage 31, the irradiation control unit 40A controls the light source driving unit 36 to irradiate the specimen 10 with the first excitation light L1 (Step S100).

As a result of the operation performed at Step S100, the specimen 10 is irradiated with the first excitation light L1. As a result of the irradiation with the first excitation light L1, the active species 26 are generated from the generating agent 18 included in the specimen 10, and the pigment compound 24 binds to the electron donor 16 of the target molecule 14 due to the active species 26 (see FIGS. 1B and 1C).

Then, the irradiation control unit 40A controls the light source driving unit 36 in such a way that the specimen 10, which has been irradiated with the first excitation light L1 at Step S100, is irradiated with the second excitation light L2 (Step S102). Meanwhile, after the operation at Step S100 is completed, the user can perform the cleansing process for cleansing the specimen 10 and then place the specimen 10 on the stage 31.

As a result of the operation performed at Step S102, the pigment compound 24 that is bound to the target molecule 14 becomes excited and produces luminescence.

Then, the obtaining unit 40B obtains a captured image of the specimen 10 from the imaging device 34 via the imaging control unit 37 (Step S104).

Subsequently, based on the captured image obtained at Step S104, the detecting unit 40C detects the pigment compound 24 that is bound to the electron donor 16 of the target molecule 14 (Step S106). It marks the end of the present routine.

As explained above, the immunostaining method according to the first embodiment includes an irradiation process. The irradiation process is a process in which the first excitation light L1 is bombarded onto the specimen 10 that includes the target molecule 14 including the electron donor 16, the antibody 20 that is bound to the target molecule 14 and that has the generating agent 18 which generates the active species 26 when irradiated with the first excitation light L1, and the pigment compound 24; and in which the active species 26 generated from the generating agent 18 due to the irradiation with the first excitation light L1 result in binding of the pigment compound 24 and the electron donor 16 of the target molecule 14.

In this way, in the immunostaining method according to the first embodiment, because of the active species 26 that are generated by bombarding the first excitation light L1 onto the generating agent 18 included in the antibody 20 which is bound to the target molecule 14, the pigment compound 24 is bound to the electron donor 16 of the target molecule 14. Hence, signal amplification in the vicinity of the target molecule 14 can be easily performed due to the pigment compound 24.

In the conventional technology, a primary antibody and a secondary antibody are sequentially made to react with the target antigen for measurement, and then an enzyme is added to the secondary antibody and a radical is generated as a result of the enzymatic reaction attributed to the enzyme. Hence, in the conventional technology, it becomes necessary to perform temperature adjustment according to the optimum temperature of the enzyme, adjustment of the reaction time according to the enzyme, and adjustment of a plurality of reaction solutions. Hence, performing immunostaining with ease is a difficult task. More specifically, in the conventional technology, there are two main issues. The first issue is that, at the time of performing a multistaining procedure, since the secondary antibody is used, the combination of the primary antibody and the secondary antibody represents the combination of the animal species that created the antibody, thereby resulting in a restriction. The other issue is that the enzymatic reaction has a different quantity of reaction products than the quantity of reaction products in the photosensitization reaction, which is attributed to the radical generation, depending on the temperature and the time; thereby making it difficult to obtain quantitativeness. Moreover, in the conventional technology, solution adjustment is not an easy task.

In contrast, in the immunostaining method according to the first embodiment, since the active species 26 are generated using the first excitation light L1, there is neither any need to perform temperature adjustment and reaction time adjustment according to the optimum temperature of the enzyme nor any need to perform adjustment of a plurality of reaction solutions, unlike in the immunostaining method using an enzyme.

Thus, the immunostaining method according to the first embodiment enables performing immunostaining with ease.

More specifically, the immunostaining method according to the first embodiment enables performing immunostaining that is excellent in achieving reduction of processes, achieving enhancement in quantitativeness, and achieving multistaining capability.

Moreover, in the immunostaining method according to the first embodiment, the amount of generation of the active species 26 can be controlled by controlling the light irradiation period, and thus the quantitativeness can be ensured. Meanwhile, the combinations of the primary antibody and the secondary antibody become limited because of the restrictions depending on the type of the immunized animal. However, in the immunostaining method according to the first embodiment, since only the primary antibody is used, multistaining becomes easier to perform because the dependency is on the number of types of the same active species 26.

Moreover, in the immunostaining method according to the first embodiment, since there is no need to use any enzyme, it becomes possible to enhance the preservability of the specimen 10, in addition to achieving the effects explained above. Furthermore, in the immunostaining method according to the first embodiment, as a result of performing immunostaining by irradiation with the first excitation light L1, it becomes possible to shorten the period of time required for immunostaining as compared to the conventional method in which an enzyme is used.

Moreover, in the immunostaining method according to the first embodiment, since the active species 26 are generated due to irradiation with the first excitation light L1, it becomes possible to selectively irradiate a particular area in the specimen 10 with the first excitation light L1. Hence, immunostaining can be selectively performed with respect to the target molecule 14 that is present in a particular area in the specimen 10.

Furthermore, in the immunostaining method according to the first embodiment, since only a primary antibody can be used as the antibody 20, it becomes possible to hold down a decrease in the signal intensity and achieve amplification and high sensitivity of the signals with ease.

Moreover, in the immunostaining method according to the first embodiment, immunostaining of the target molecule 14 is performed by irradiating it with the first excitation light L1. Hence, by adjusting the quantity of light (at least either the light intensity or the irradiation period); the amount of binding of the pigment compound 24 to the target molecule 14 can be adjusted with ease.

Thus, in addition to enabling achieving the effects explained earlier, the immunostaining method according to the first embodiment enables achieving enhancement in the quantitativeness in the detection of the target molecule 14.

Second Embodiment

In a second embodiment, the explanation is given for a way of implementing a multistaining procedure by repeatedly performing the irradiation process according to the first embodiment, while varying the wavelength of the first excitation light L1.

In the immunostaining method according to the second embodiment, a plurality of types of target molecules 14 are stabilized on the solid phase 12, and a plurality of types of antibodies 20 including mutually different generating agents 18 are respectively bound to the corresponding types of target molecules 14. Then, in each instance of performing the irradiation process, the wavelength range of the first excitation light L1 and the type of the pigment compound 24 are varied.

FIG. 5 is a schematic diagram illustrating an example of a specimen 11. The specimen 11 that is used in the immunostaining method according to the second embodiment includes a plurality of types of target molecules 14. In FIG. 5 is illustrated an example in which three types of target molecules, namely, target molecules 14A, 14B, and 14C are present. Alternatively, in the specimen 11, there can be two types of target molecules 14 or there can be four or more types of target molecules 14.

The types of target molecules (the target molecules 14A, 14B, and 14C) have specificity against mutually different types of antibodies 20.

In FIG. 5 is illustrated an example in which an antibody 20A has specificity against the target molecule 14A, an antibody 20B has specificity against the target molecule 14B, and an antibody 20C has specificity against the target molecule 14C.

The plurality of types of antibodies 20 (the antibodies 20A, 20B, and 20C) include mutually different types of generating agents 18. In the second embodiment, the explanation is given for an example in which the antibody 20A includes a generating agent 18A, the antibody 20B includes a generating agent 18B, and the antibody 20C includes a generating agent 18C.

The plurality of types of generating agents 18 (the generating agents 18A, 18B, and 18C) become excited when irradiated with the first excitation light L1 having mutually different wavelength ranges, and generate the active species 26. That is, the plurality of types of generating agents 18 become excited when irradiated with the first excitation light L1 having mutually non-overlapping wavelength ranges, and generate the active species 26.

In the second embodiment, a repetition process is performed in which the irradiation process according to the first embodiment is repeatedly performed by varying the wavelength range of the first excitation light L1 and the type of the pigment compound 24.

Herein, varying the type of the pigment compound 24 implies adding the pigment compound 24 having at least either different absorption or a different emission spectrum. More particularly, varying the type of the pigment compound 24 implies adding the pigment compound 24 having at least either a different color, or different fluorescence, or different phosphorescence. That is, during the repetition process, in each instance of performing the irradiation process, the same specimen 11 is added with the pigment compound 24 having a different color than the color of the pigment compound 24 that was added in the previous instance of the irradiation process.

That is, in the immunostaining method according to the second embodiment, after stabilizing the plurality of types of target molecules 14 (the target molecules 14A, 14B, and 14C) on the solid phase 12, the plurality of types of antibodies 20 (the antibodies 20A, 20B, and 20C) including mutually different generating agents 18 are respectively bound to the corresponding types of target molecules 14. Then, in each instance of performing the irradiation process, the wavelength range of the first excitation light L1 and the type of the pigment compound 24 are varied.

Alternatively, after stabilizing the plurality of types of target molecules 14 (the target molecules 14A, 14B, and 14C) on the solid phase 12; in each instance of performing the irradiation process, the type of the antibody 20, the wavelength range of the first excitation light L1, and the type of the pigment compound 24 can all be varied.

FIG. 6 is an explanatory diagram for explaining a sequence of processes performed in the immunostaining method according to the second embodiment. As illustrated in FIG. 6, in the immunostaining method according to the second embodiment, firstly, in an identical manner to the first embodiment, the preprocessing is performed (Step S200) and that is followed by the antigen-antibody reaction process (Step S202), the irradiation process (Step S204), the cleansing process (Step S206), and the detection process (Step S208) in that order. However, in the immunostaining method according to the second embodiment, the irradiation process at Step S204, the cleansing process at Step S206, and the detection process at Step S208 are repeatedly performed for the number of times equal to the number of types of target molecules 14 included in the specimen 11, while varying the wavelength range of the first excitation light L1 and the type of the pigment compound 24.

Given below is the explanation of a specific example of the repetition process according to the second embodiment.

In the following specific example, the explanation is given about the case in which, in each instance of performing the irradiation process, the wavelength area of the first excitation light L1 and the type of the pigment compound 24 is varied. Moreover, in the following specific example, the explanation is given about the case in which the irradiation process is repeated thrice.

[Preprocessing/Antigen-Antibody Reaction Process]

Figure 7A:
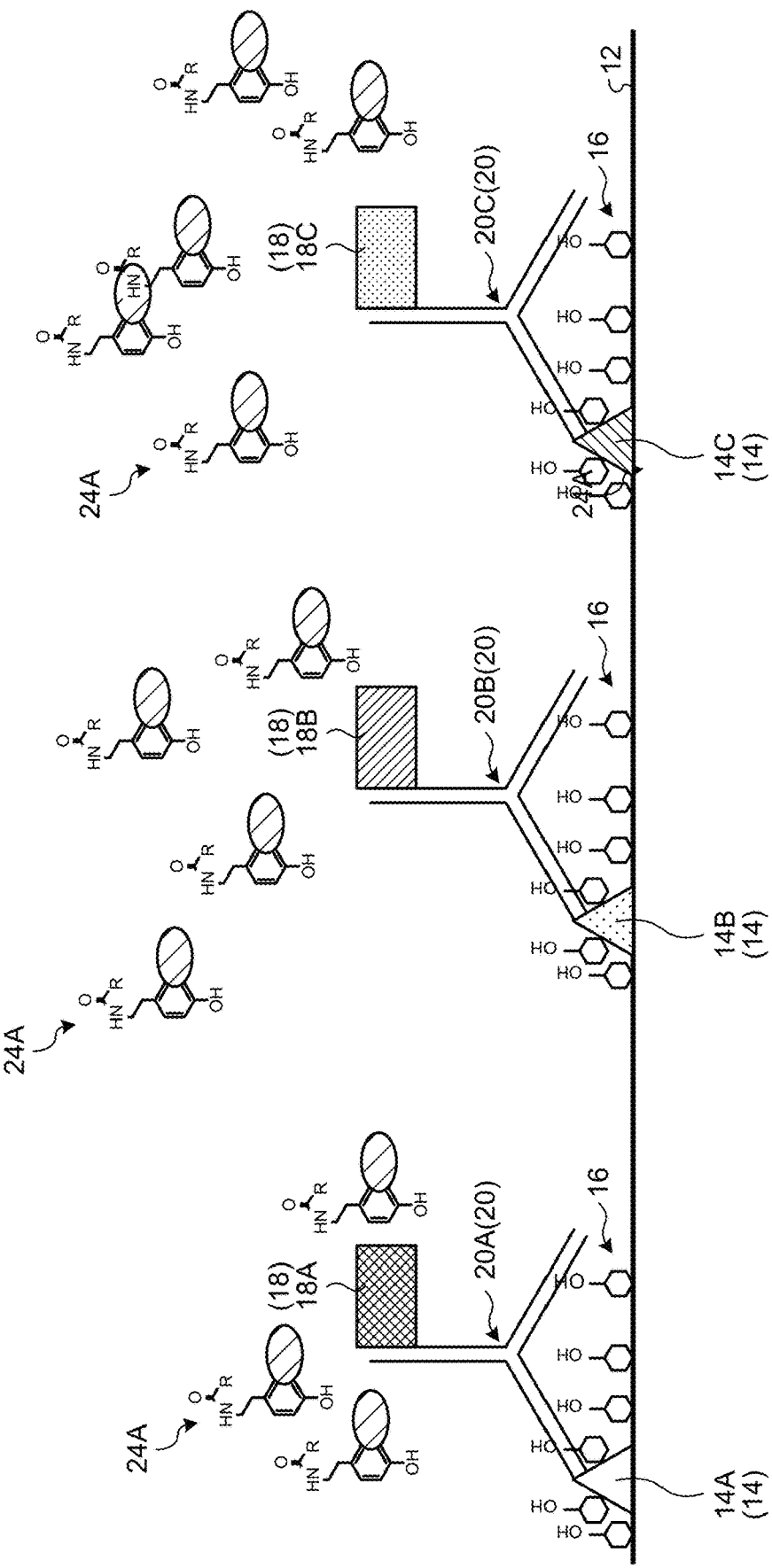
FIG. 7A is a schematic diagram illustrating an example of the specimen according to the second embodiment of the application concerned.

FIG. 7A is a schematic diagram illustrating an example of the specimen 11. In an identical manner to the first embodiment, firstly, the preprocessing is performed. For example, the solid phase 12 is prepared on which the target molecules 14A, 14B, and 14B are stabilized. Then, in an identical manner to the first embodiment, the activation process is performed for activating the target molecules 14; and that is followed by the blocking process.

Subsequently, the antigen-antibody reaction process is performed. That is, the plurality of types of antibodies 20 (the antibodies 20A, 20B, and 20C) including mutually different types of generating agents 18A are respectively bound to the corresponding types of target molecules 14 (the target molecules 14A, 14B, and 14B). More specifically, as illustrated in FIG. 7A, the antibody 20A, which has specificity against the target molecule 14A from among the plurality of types of target molecules 14, is bound to the target molecule 14A. The antibody 20A has the generating agent 18A bound thereto. Moreover, the antibody 20B, which has specificity against the target molecule 14B, is bound to the target molecule 14B. The antibody 20B has the generating agent 18B bound thereto. Furthermore, the antibody 20C, which has specificity against the target molecule 14C, is bound to the target molecule 14C. The antibody 20C has the generating agent 18C bound thereto.

[Irradiation Process (First Instance)]

In the irradiation process, firstly, the pigment compound 24 is added. In FIG. 7A, it is illustrated that a pigment compound 24A is added as the pigment compound 24.

FIG. 7B is an explanatory diagram for explaining irradiation with a first excitation light Lia. As illustrated in FIG. 7B, the specimen 11 is irradiated with the first excitation light Lia serving as the first excitation light L1. The first excitation light Lia is the light having such a wavelength range that the generating agent 18A bound to the antibody 20A generates the active species 26. Hence, as a result of getting irradiated with the first excitation light Lia, the generating agent 18A generates the active species 26.

FIG. 7C is an explanatory diagram for explaining the state in which the pigment compound 24A is bound to the target molecule 14A. As illustrated in FIG. 7C, due to the action of the active species 26 that are generated in the vicinity of the generating agent 18A in the antibody 20A which is bound to the target molecule 14A, the pigment compound 24A selectively binds to the electron donor 16 of the target molecule 14A.

[Cleansing Process]

Subsequently, the cleansing process is performed. The cleansing process is identical to that explained in the first embodiment. As a result of performing the cleansing process, the unreacted pigment compound 24A is removed from the specimen 11.

[Detection Process (First Instance)]

Then, the color of the pigment compound 24A is measured or observed, and the target molecule 14A is detected.

[Irradiation Process (Second Instance)]

FIG. 8A is a schematic diagram illustrating an example of the specimen 11. As illustrated in FIG. 8A, subsequently, the pigment compound 24 is added. In FIG. 8A, it is illustrated that a pigment compound 24B is added as the pigment compound 24. As long as the pigment compound 24B is the pigment compound 24 having a different color than the pigment compound 24A bound to the target molecule 14A, it serves the purpose.

Figure 8B:
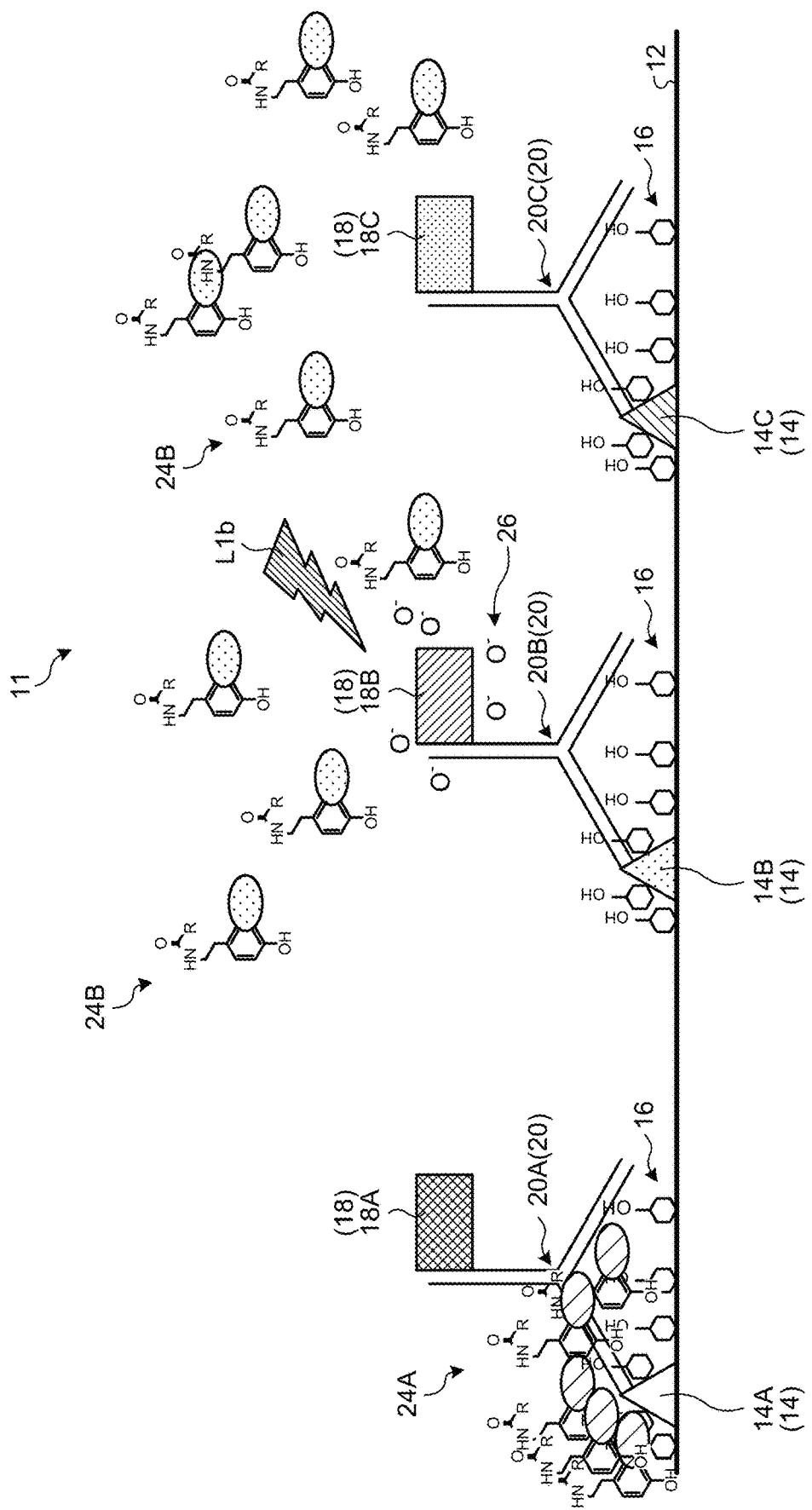
FIG. 8B is an explanatory diagram for explaining irradiation with a first excitation light according to the second embodiment of the application concerned.

FIG. 8B is an explanatory diagram for explaining irradiation of a first excitation light Lib. As illustrated in FIG.

8B, the specimen 11 is irradiated with the first excitation light L1b serving as the first excitation light L1. The first excitation light L1b is the light having such a wavelength range that the generating agent 18B bound to the antibody 20B generates the active species 26. Hence, as a result of getting irradiated with the first excitation light L1b, the generating agent 18B generates the active species 26. Herein, it is desirable that the first excitation light L1b has a longer wavelength range than the wavelength range of the first excitation light L1a bombarded in the previous instance of the irradiation process.

FIG. 8C is an explanatory diagram for explaining the state in which the pigment compound 24B is bound to the target molecule 14B. As illustrated in FIG. 8C, due to the action of the active species 26 that are generated in the vicinity of the generating agent 18B in the antibody 20A which is bound to the target molecule 14B, the pigment compound 24B selectively binds to the electron donor 16 of the target molecule 14B.

[Cleansing Process]

Subsequently, the cleansing process is performed. The cleansing process is identical to that explained in the first embodiment. As a result of performing the cleansing process, the unreacted pigment compound 24B is removed from the specimen 11.

[Detection Process (Second Instance)]

Then, the color of the pigment compound 24B is measured or observed, and the target molecule 14B is detected.

[Irradiation Process (Third Instance)]

FIG. 9A is a schematic diagram illustrating an example of the specimen 11. As illustrated in FIG. 9A, subsequently, the pigment compound 24 is added. In FIG. 9A, it is illustrated that a pigment compound 24C is added as the pigment compound 24. As long as the pigment compound 24C is the pigment compound 24 having a different color than the pigment compound 24A bound to the target molecule 14A and the pigment compound 24B bound to the target molecule 14B, it serves the purpose.

FIG. 9B is an explanatory diagram for explaining irradiation of a first excitation light L1c. As illustrated in FIG. 9B, the specimen 11 is irradiated with the first excitation light L1c serving as the first excitation light L1. The first excitation light L1c is the light having such a wavelength range that the generating agent 18C bound to the antibody 20C generates the active species 26. Hence, as a result of getting irradiated with the first excitation light L1c, the generating agent 18C generates the active species 26. Herein, it is desirable that the first excitation light L1c has a longer wavelength range than the wavelength range of the first excitation light L1b bombarded in the previous instance of the irradiation process.

FIG. 9C is an explanatory diagram for explaining the state in which the pigment compound 24C is bound to the target molecule 14C. As illustrated in FIG. 9C, due to the action of the active species 26 that are generated in the vicinity of the generating agent 18C in the antibody 20C which is bound to the target molecule 14C, the pigment compound 24C selectively binds to the electron donor 16 of the target molecule 14C.

[Cleansing Process]

Subsequently, the cleansing process is performed. The cleansing process is identical to that explained in the first embodiment. As a result of performing the cleansing process, the unreacted pigment compound 24C is removed from the specimen 11.

[Detection Process (Third Instance)]

Then, the color of the pigment compound 24C is measured or observed, and the target molecule 14C is detected.

Meanwhile, as far as the detection process is concerned, after the irradiation process and the cleansing process are performed for the number of times equal to the number of types of target molecules 14, the detection process can be performed in one go at the last.

Moreover, in the case of performing the irradiation process in a repeated manner, it is desirable to adjust the wavelength range of the first excitation range L1, which is bombarded during the irradiation process, in such a way that, latter the instance of the irradiation process during which the first excitation light L1 is bombarded, the longer is the wavelength of the first excitation light L1.

As explained above, in the immunostaining method according to the second embodiment, multistaining is performed by repeatedly performing the irradiation process for the number of times equal to the number of types of target molecules 14 included in the specimen 11, while varying the wavelength range of the first excitation light L1 and the type of the pigment compound 24.

Thus, in the immunostaining method according to the second embodiment, multistaining can be performed with ease, in addition to achieving the effects explained earlier.

Moreover, as described above, in the immunostaining method according to the second embodiment, in the state in which the plurality of types of target molecules 14 (the target molecules 141, 14B, and 14C) included in the specimen 11 are respectively bound to the corresponding antibodies 20 (the antibodies 20A, 20B, and 20C), the irradiation process can be repeatedly performed by varying the wavelength range of the first excitation light L1 and the type of the pigment compound 24. Thus, just by varying the wavelength range of the first excitation light L1 to be bombarded onto the specimen 11 and by varying the type of the pigment compound 24, the target molecules 14 can be easily stained with the colors corresponding to the types thereof.

Working Example

Given below is the specific explanation of the application concerned with reference to working examples. However, the application concerned is not limited to the working examples explained below.

First Working Example

—Preprocessing, Antigen-Antibody Reaction Process, Irradiation Process, Cleansing Process—

A glass slide was kept ready as the solid phase 12. Moreover, a paraffin-embedded pathology specimen was kept ready as the specimen including a plurality of types of target molecules 14. Then, on the solid phase 12, the paraffin-embedded pathology specimen was cut into thin slices of 4 um, subjected to heat, and stabilized on the glass slide; and that was followed by deparaffinization. Subsequently, the pathology specimen was heated to 95° C. in a microwave oven, and the target molecules 14 were activated. Then, using 100 μl to 400 μl of a block solution (TBST/5% normal goat serum: 1×solution formed by adding 250 μl of normal goat serum in 5 ml of TBST), the solid phase 12 was blocked for one hour at room temperature.

Then, an FITC-bound primary antibody (by Molecular Probes) was kept ready as the antibody 20 including the generating agent 18. Then, the solution of the antibody 20 was added to the solid phase 12 on which the pathogen specimen was stabilized, and the mixture was kept as it is for two hours at room temperature. As a result, the antibody 20 was bound to the target molecule 14.

Subsequently, as the pigment compound 24, regarding the Cy3-bound tyramide compound (by Perkin-Elmer Corporation), a reaction solution formed by diluting a stock solution by 50 times using a 1× Plus application diluting solution was added to the solid phase 12.

Then, as the first excitation light L1 having such a wavelength range that the generating agent 18 generates the active species 26, the first excitation light L1 having the wavelength range of 488 nm±10 nm was bombarded for five minutes.

Subsequently, while stirring the specimen 10 inside a TNT buffer, cleansing for five minutes at room temperature was repeatedly performed for three times, and the unreacted pigment compound 24 was removed.

—Detection Process—

In the state in which the second excitation light L2 having the wavelength of 550 nm±10 nm was being bombarded onto the specimen 10 that had been already cleansed, the specimen 10 was captured in an image and the captured image was obtained. Then, the number of luminescent spots in the captured image was measured. The measurement of the number of luminescent spots was performed using the ImageJ FindMaxima method (in which the irradiation period is of 200 msec, and NoiseTolerance is 60). Moreover, regarding the second excitation light L2 bombarded onto the specimen at the time of obtaining the captured image, the energy was set to be equal to 1000 mW/cm$^2$.

Figure 10:
FIG. 10 is a diagram illustrating an image indicating the detection result according to the first embodiment of the application concerned.

As a result, an image illustrated in FIG. 10 was obtained. In the first working example, an image was obtained in which the luminescent points were green in color. Thus, it could be confirmed that immunostaining, which is excellent in achieving reduction of processes and achieving enhancement in quantitativeness, can be performed and that too with ease.

Second Working Example

In the first working example, the same pathogen specimen was used as used in the first working example; the first excitation light having the wavelength of 581 nm±10 nm was used; a Cy3.5-bound primary antibody was used as the antibody 20A having the generating agent 18A bound thereto; the Cy5-bound tyramide was used as the pigment compound 24; and the second excitation wavelength was equal to 648 nm±10 nm. Apart from that, the preprocessing, the antigen-antibody reaction process, the irradiation process, and the detection process were performed in an identical manner to the first working example.

As a result, an image was obtained that was identical to the image illustrated in FIG. 10. In the second working example, an image was obtained in which the luminescent points were purple in color. Thus, it could be confirmed that immunostaining, which is excellent in achieving reduction of processes and achieving enhancement in quantitativeness, can be performed and that too with ease.

Third Working Example

In a third working example, a multistaining procedure was performed. More particularly, in an identical manner to the first working example, a paraffin-embedded pathology specimen was kept ready as the specimen including a plurality of types of target molecules 14. Then, the preprocessing and the antigen-antibody reaction process were performed in an identical manner to the first working example. Then, the irradiation process, the cleansing process, and the detection process were performed according to the first working example. Subsequently, the irradiation process, the cleansing process, and the detection process were performed according to the second working example.

As a result, in the first instance of performing the preprocessing and the detection process, the obtained image had green luminescent points. Moreover, in the second instance of performing the preprocessing and the detection process, the obtained image had purple luminescent points. Thus, it could be confirmed that immunostaining, which is excellent in achieving reduction of processes, achieving enhancement in quantitativeness, and achieving multistaining capability, can be performed; and multistaining can be performed with ease.

Meanwhile, a configuration as explained below also falls within the technical scope of the application concerned.

(1)

An immunostaining method comprising an irradiation process that includes irradiating, with a first excitation light, a specimen which includes a target molecule including electron donor, an antibody that is bound to the target molecule and that includes a generating agent for generating active species when irradiated with the first excitation light, and a pigment compound, and causing binding of the pigment compound and the electron donor due to active species generated from the generating agent when irradiated with the first excitation light.

(2)

The immunostaining method according to (1), wherein the first excitation light has such wavelength range that the generating agent generates active species but the pigment compound does not generate active species.

(3)

The immunostaining method according to (1) or (2), wherein the pigment compound becomes excited when irradiated with a second excitation light, and the first excitation light and the second excitation light have different wavelength ranges.

(4)

The immunostaining method according to (3), wherein the first excitation light has longer wavelength range than the second excitation light.

(5)

The immunostaining method according to any one of (1) to (4), wherein the pigment compound is a pigment-labeled aromatic compound.

(6)

The immunostaining method according to any one of (1) to (5), wherein the electron donor is an aromatic compound having a polar group.

(7)

The immunostaining method according to any one of (1) to (6), wherein the electron donor is a compound that has a radical crosslinking reaction with the pigment compound due to active species.

(8)

The immunostaining method according to any one of (1) to (7), wherein the generating agent is a cyanine pigment.

(9)

The immunostaining method according to any one of (1) to (8), wherein the pigment compound is a tyramide pigment.

(10)

The immunostaining method according to any one of (1) to (9), wherein the target molecule either is an antigen having specificity against the antibody or is a primary antibody bound to the antigen.

(11)

The immunostaining method according to any one of (1) to (10), further comprising a repetition process that includes repeatedly performing the irradiation process, in which the specimen including a plurality of types of the target molecule is irradiated with the first excitation light, while varying wavelength range of the first excitation light and type of the pigment compound.

(12)

An immunostaining system comprising:

an irradiating unit that irradiates, with a first excitation light, a specimen which includes a target molecule including electron donor, an antibody that is bound to the target molecule and that includes a generating agent for generating active species when irradiated with the first excitation light, and a pigment compound; and a detecting unit that detects the pigment compound which is bound to the electron donor.

(13)

An immunostaining kit comprising:

an antibody that is bound to a target molecule including electron donor and that includes a generating agent for generating active species when irradiated with a first excitation light; and a pigment compound, wherein due to active species generated from the generating agent when irradiated with the first excitation light, there occurs binding of the electron donor and the pigment compound.

REFERENCE SIGNS LIST 10, 11 specimen
14, 14A, 14B, 14C target molecule
16 electron donor
18 generating agent
20, 20A, 20B, 20C antibody
24, 24A, 24B, 24C pigment compound
26 active species

The invention claimed is:

1. An immunostaining method comprising an irradiation process that includes irradiating, with a first excitation light, a specimen which includes a target molecule including electron donor, an antibody that is bound to the target molecule and that includes a generating agent for generating active species when irradiated with the first excitation light, and a pigment compound, and causing binding of the pigment compound and the electron donor due to active species generated from the generating agent when irradiated with the first excitation light.

2. The immunostaining method according to claim 1, wherein the first excitation light has such wavelength range that the generating agent generates active species but the pigment compound does not generate active species.

3. The immunostaining method according to claim 1, wherein the pigment compound becomes excited when irradiated with a second excitation light, and the first excitation light and the second excitation light have different wavelength ranges.

4. The immuno staining method according to claim 3, wherein the first excitation light has longer wavelength range than the second excitation light.

5. The immunostaining method according to claim 1, wherein the pigment compound is a pigment-labeled aromatic compound.

6. The immunostaining method according to claim 1, wherein the electron donor is an aromatic compound having a polar group.

7. The immuno staining method according to claim 1, wherein the electron donor is a compound that has a radical crosslinking reaction with the pigment compound due to active species.

8. The immuno staining method according to claim 1, wherein the generating agent is a cyanine pigment.

9. The immunostaining method according to claim 1, wherein the pigment compound is a tyramide pigment.

10. The immunostaining method according to claim 1, wherein the target molecule either is an antigen having specificity against the antibody or is a primary antibody bound to the antigen.

11. The immuno staining method according to claim 1, further comprising a repetition process that includes repeatedly performing the irradiation process, in which the specimen including a plurality of types of the target molecule is irradiated with the first excitation light, while varying wavelength range of the first excitation light and type of the pigment compound.

12. An immunostaining system comprising:

an irradiating unit that irradiates, with a first excitation light, a specimen which includes a target molecule including electron donor, an antibody that is bound to the target molecule and that includes a generating agent for generating active species when irradiated with the first excitation light, and a pigment compound; and a detecting unit that detects the pigment compound which is bound to the electron donor.

13. An immunostaining kit comprising:

an antibody that is bound to a target molecule including electron donor and that includes a generating agent for generating active species when irradiated with a first excitation light; and a pigment compound, wherein due to active species generated from the generating agent when irradiated with the first excitation light, there occurs binding of the electron donor and the pigment compound.

* * * * *